(12) United States Patent
Zhang et al.

(10) Patent No.: US 11,401,320 B2
(45) Date of Patent: Aug. 2, 2022

(54) QTY FC FUSION RECEPTOR PROTEINS

(71) Applicants: Massachusetts Institute of Technology, Cambridge, MA (US); Avalon GloboCare Corp., Freehold, NJ (US)

(72) Inventors: Shuguang Zhang, Cambridge, MA (US); David Jin, Staten Island, NY (US); Rui Qing, Somerville, MA (US); Uwe Sleytr, Vienna (AT)

(73) Assignees: Massachusetts Institute of Technology, Cambridge, MA (US); Avalong GloboCare Corp., Freehold, NJ (US)

( * ) Notice: Subject to any disclaimer, the term of this patent is extended or adjusted under 35 U.S.C. 154(b) by 0 days.

(21) Appl. No.: 17/210,878

(22) Filed: Mar. 24, 2021

(65) Prior Publication Data
US 2021/0309720 A1   Oct. 7, 2021

Related U.S. Application Data

(60) Provisional application No. 63/048,730, filed on Jul. 7, 2020, provisional application No. 63/002,666, filed on Mar. 31, 2020.

(51) Int. Cl.
*C07K 14/715*  (2006.01)
*A61K 45/06*  (2006.01)
*A61K 38/17*  (2006.01)
*A61K 38/00*  (2006.01)

(52) U.S. Cl.
CPC ........ *C07K 14/7158* (2013.01); *A61K 38/177* (2013.01); *A61K 45/06* (2013.01); *A61K 38/00* (2013.01); *C07K 2319/03* (2013.01); *C07K 2319/30* (2013.01)

(58) Field of Classification Search
CPC .................................................. C07K 14/7158
See application file for complete search history.

(56) References Cited

U.S. PATENT DOCUMENTS

| | | |
|---|---|---|
| 8,637,452 B2 | 1/2014 | Zhang et al. |
| 9,309,302 B2 | 4/2016 | Zhang et al. |
| 9,884,915 B2 | 2/2018 | Chamorro Perez et al. |
| 10,035,837 B2 | 7/2018 | Zhang et al. |
| 10,373,702 B2 | 8/2019 | Zhang et al. |
| 2012/0252719 A1 | 10/2012 | Zhang et al. |
| 2014/0243277 A1 | 8/2014 | Zhang et al. |
| 2015/0370960 A1 | 12/2015 | Zhang et al. |
| 2015/0370961 A1 | 12/2015 | Zhang et al. |
| 2016/0264640 A1 | 9/2016 | Zhang et al. |
| 2017/0344699 A1 | 11/2017 | Zhang et al. |
| 2018/0118806 A1 | 5/2018 | Zhang et al. |
| 2018/0312562 A1 | 11/2018 | Zhang et al. |
| 2019/0353654 A1 | 11/2019 | Zhang et al. |
| 2020/0176073 A1 | 6/2020 | Zhang et al. |

FOREIGN PATENT DOCUMENTS

WO    2007113285 A2    10/2007

OTHER PUBLICATIONS

Zhang, S. et al., "QTY code enables design of detergent-free chemokine receptors that retain ligand-binding activities", Proc. Natl. Acad. Sci. USA, vol. 115, No. 37, 2018, E8652-E8659.

*Primary Examiner* — Prema M Mertz
(74) *Attorney, Agent, or Firm* — Elmore Patent Law Group, P.C.; Carolyn Elmore

(57) ABSTRACT

The present invention is directed to QTY CCR9 and CXCR2 variant Fc receptor fusion proteins, methods for the preparation thereof and methods of use thereof.

3 Claims, 5 Drawing Sheets
Specification includes a Sequence Listing.

QTY FC FUSION RECEPTOR PROTEINS

RELATED APPLICATIONS

This application claims the benefit of U.S. Provisional Application No. 63/002,666 filed Mar. 31, 2020 and U.S. Provisional Application No. 63/048,730 filed Jul. 7, 2020. The entire teachings of the above-referenced applications are incorporated herein by reference.

BACKGROUND OF THE INVENTION

Chimeric antigen receptor (CAR) T-cell therapy is a cellular immunotherapy in which patient's T cells are engineered in vitro to target and eliminate cancer cells in vivo. In CAR-T treatment, the T cells from a patient's blood are extracted by apheresis. The gene for a specific receptor (CAR) which binds to a certain tumor target is delivered to the T cells by viral vector or non-viral transposon methods (Ittershagen et al., 2019; Jain & Davila, 2018; Srivastava & Riddell, 2015). At present, two anti-CD19 CAR-T products have been approved by the US FDA for the treatment of B-cell acute lymphoblastic leukemia and non-Hodgkin lymphoma; CAR-T therapy for other cancer types undergoing vigorous clinical studies. CAR-T therapy holds great promise for treating hematologic malignancies, and recent clinical evidence has indicated that similar approaches can also be used to treat solid tumors (Baybutt et al., 2019).

However, there are several side effects during CAR-T treatment that is potentially fatal to the patients, including: cytokine release syndrome (CRS), neurologic events, neutropenia and anemia (Xu & Tang, 2014). Among all the side effects, CRS is considered as a significant one that can be life-threatening. Cytokines are immune mediators essential in many bodily actions in human. Yet, a large and rapid release of cytokines into the blood from immune cells can induce "cytokine storm" ("CRS"). Most patients with CRS develop a mild flu-like reaction such as fever, fatigue, headache and rash. However, the reaction may progress to an uncontrolled, systemic inflammatory response with extreme pyrexia and become life-threatening (Shimabukuro-Vornhagen et al., 2018).

Manifestation of CRS can also be triggered by bacterial and viral infections such as influenza and hepatitis virus (de Jong et al., 2006; Savarin & Bergmann, 2018; Tisoncik et al., 2012). The current COVID-19 (Coronavirus Disease 2019) global pandemic involves CRS in many stages of its pathological course that causes lung fibrosis, acute respiratory distress syndrome, and eventually leads to multiple organ failure (Huang et al., 2020; Xu et al., 2020). Other conditions, including graft-versus-host disease, sepsis, Ebola, avian influenza, smallpox, and systemic inflammatory response syndrome, also involve extensive release of undesired cytokines (Drazen, 2000).

Fc fusion proteins, an immunoglobulin Fc region directly linked to, for example, an extracellular domain of a receptor, are therapeutic agents that can bind and eliminate ligands. An example of a fusion protein is etanercept, an anti-TNF drug currently marketed as a treatment for a variety of inflammatory diseases. Although the therapeutic protein has been found to be safe and effective, the utilization of the molecule is limited by an unexpected short serum half-life (80-120 hours about 4 days) when administered by subcutaneous injection. Other attempts to develop Fc fusion proteins to clear aberrant protein expression has been limited. However, improved strategies for Fc fusion protein design is needed. Early treatment of sepsis, for example, includes the use of timely, appropriate antibiotics, intravenous fluids, oxygen therapy as well as vasopressor and inotropic support where needed. Other additional treatments including extracorporeal or so-called blood purification techniques (BPT) have been tried (Zhou et al., Blood Purification and Mortality in Sepsis: a meta-analysis of randomized trials. Crit. Care Med. 2013; 11, 507-13. These techniques include (among others): hemofiltration, hemoperfusion, intermittent or continuous high-volume hemofiltration, plasmapheresis or adsorption. The rationale behind such an approach is to achieve "immune homeostasis" which theoretically reduces the potential danger caused by dysregulation of the host response to infection. This may be heralded by a profound rise in inflammatory mediators, including cytokines which contribute to the dramatic systemic effects of sepsis, mainly in septic shock.

SUMMARY OF THE INVENTION

The application provides novel Fc fusion water soluble GPCR proteins with QTY membrane regions.

The applicants have previously devised a novel tool called "QTY code" which regulates the water solubility of redesigned membrane proteins through pairwise substituting hydrophobic amino acids with hydrophilic ones (U.S. Pat. No. 8,637,452 and WO2015/148820 (Zhang et al.) and Zhang et al., 2018, *QTY code enables design of detergent-free chemokine receptors that retain ligand-binding activities. Proc Natl Acad Sci USA,* 115(37), E8652-E8659). Hydrophobic amino acids Leu, Val, Ile and Phe are exchanged by hydrophilic Gln, Thr and Tyr in the transmembrane regions of a receptor, based on the structural and electron density maps similarity in their side chains. The QTY code has provided flexibility in studying the physiological and functional properties of GPCRs, as well as promoting their utilization, without the requirements of time consuming and expensive detergent screening or use of nanodisks.

The applicants reported the QTY code design of cytokine receptors comprising an Fc domain, QTY transmembrane regions and extracellular domains of chemokine receptors, including CCR9 and CXCR2. These QTY code designed GPCRs show ligand-binding properties similar to their counterpart native receptors without the presence of hydrophobic patches. The exemplified receptors were fused with Fc domain of mouse IgG2a protein to form an antibody-like structure. These Fc-fusion receptors were expressed and purified in an *E. coli* system with sufficient yield (~mg/L) in LB media. We also showed that the binding affinity of these QTY receptors approximated isolated native receptors on solution-based assays. These QTY code design of functional, water-soluble Fc-fusion GPCR proteins can be used clinically as decoy therapy to rapidly remove excessive cytokines in the setting of hyperactive immune reactions during CRS or "cytokine storm". In addition, the proteins of the invention can be used ex vivo or extracorporeally to remove cytokines from human blood. The present invention includes a method for the reduction in cytokine levels through the use of a new sorbent technology. The sorbent material can be coated with water soluble GPCRs directed to specific signaling molecules (e.g., cytokines such as interferon, interleukin, chemokines) with or without the use of S-layer proteins for anchoring the GPCRs. Optionally, the sorbent material can be in a cartridge and can have a variety of forms, including for example, polymer beads, glass beads, magnetic beads, porous polymers, and membranes. The blood, characterized by reduced cytokine and/or chemokine levels, can optionally be administered to the patient. The bound cytokines and/or chemokines can be detected on the sorbent, thereby being useful as a diagnostic. The bound cytokines and/or chemokines can optionally be recovered from the sorbent.

The invention includes QTY Fc Fusion proteins comprising an Fc domain or fragment thereof, a QTY GPCR. For example, the Fc fusion proteins of the invention can have the formula:

N-terminus(QTY GPCR-Fc-Domain) C-terminus

Each domain or region can be directly or indirectly linked or fused to its adjacent domain. For example, additional peptide linkers (one or more glycine residues or restriction sites) can be used to link domains. Additional domains (such as an immunoglobulin hinge region, restriction sites, or tags) can also be used.

The invention also includes pharmaceutical compositions comprising Fc fusion QTY GPCR proteins, methods of manufacture and methods of use.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
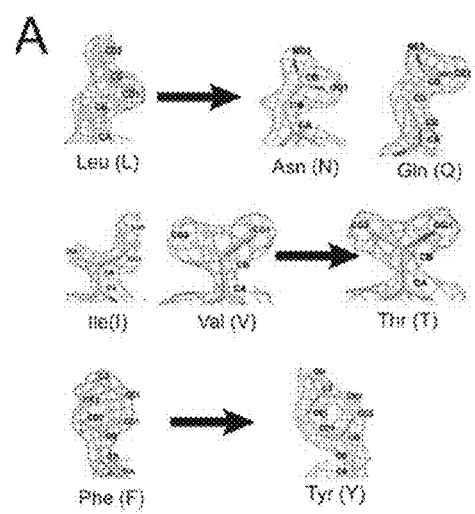
FIGS. 1A and 1B illustrate the QTY strategy wherein the amino acids Q, T and Y, together with other amino acids, can form alpha helical domains that mimic a transmembrane region. (A) Crystallographic electronic density maps of the following amino acids: Leucine (L), Asparagine (N), Glutamine (Q), Isoleucine (I), Valine (V), Threonine (T), Phenylalanine (F) and Tyrosine (Y). The density maps of L, N and Q are very similar. Likewise, the density maps of I, V and T are similar, and the density maps of F and Y are similar. (B) Helical wheels before and after applying the QTY code to transmembrane helical segment 1 (TM1) of CXCR2. Amino acids that interact with water molecules are light blue in color. The QTY code conversions render the alpha-helical segment water-soluble.
Figure 1B:
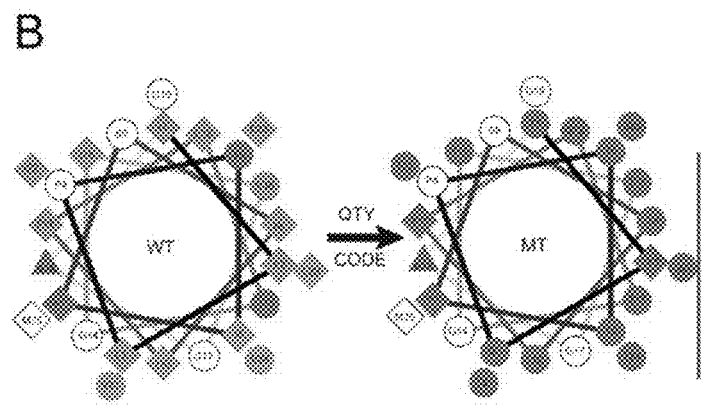
Figure 2A:
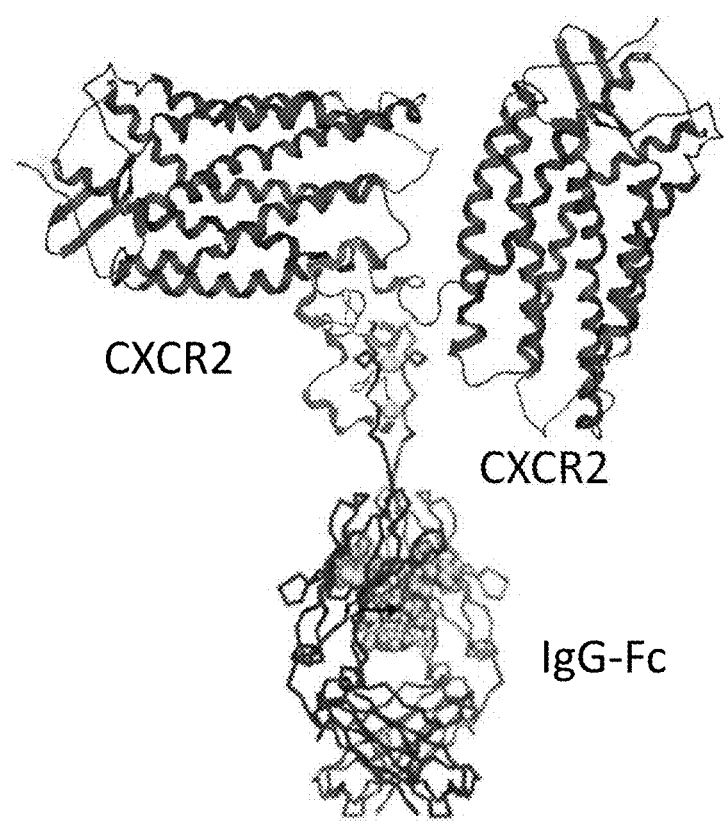
FIGS. 2A and 2B. Schematic illustration for Fc fused QTY variant cytokine receptors with antibody-like structure. (A) CXCR2$^{QTY}$-Fc and (B) CCR9$^{QTY}$-Fc. These illustrations are not to scale and the receptors parts are significantly emphasized for clarity.
Figure 2B:
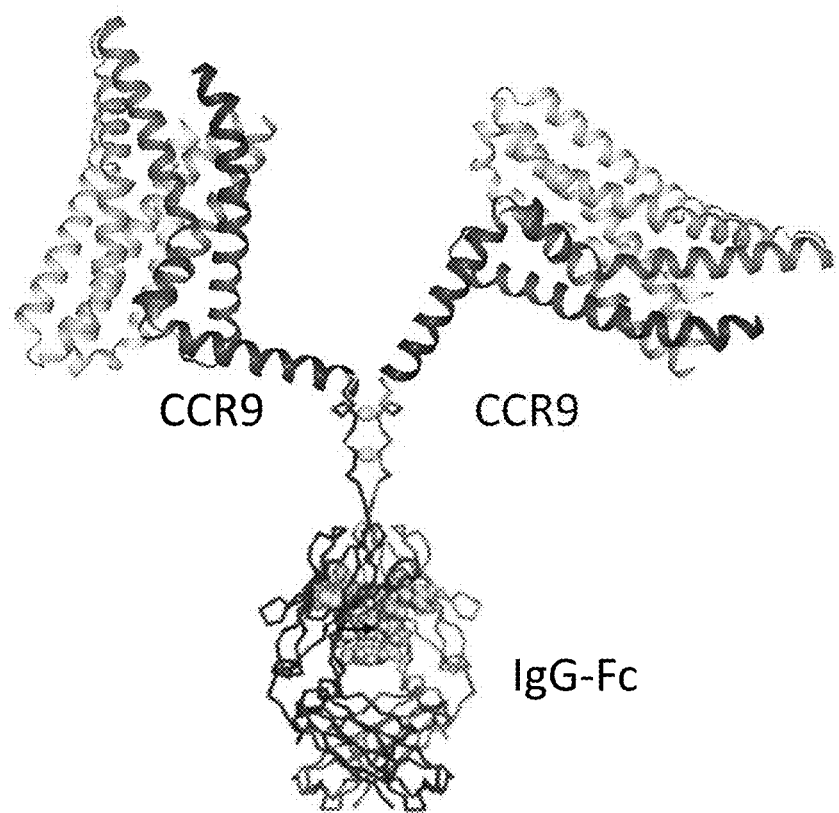
Figure 3A:
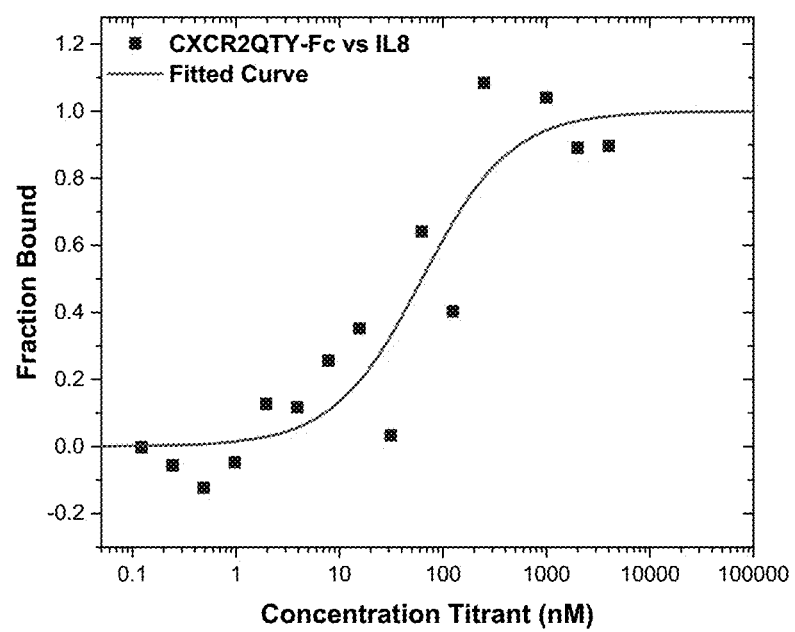
FIGS. 3A and 3B. MST ligand binding measurements. The receptors were labeled with fluorescent dye. The ligands were purchased commercially from and dissolved in di water. (A) CXCR2$^{QTY}$-Fc with IL8 and (B) CCR9$^{QTY}$-Fc with CCL25.
Figure 3B:
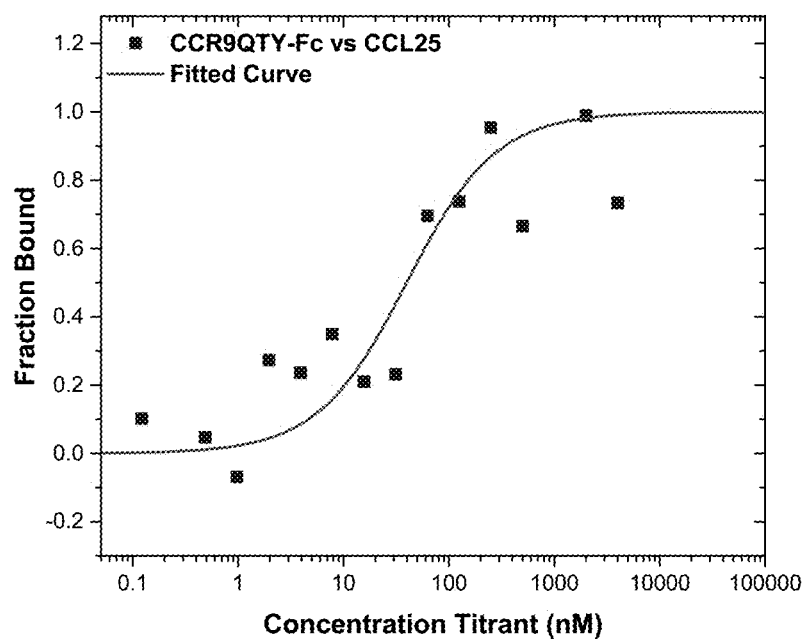

A description of preferred embodiments of the invention follows.

QTY Transmembrane Domain

The invention encompasses a modified, synthetic, and/or non-naturally occurring, α-helical domain(s) and water-soluble polypeptide (e.g., "GPCR$^{QTY}$") comprising such modified α-helical domain(s), wherein the modified α-helical domain(s) comprise an amino acid sequence in which a plurality of hydrophobic amino acid residues (L, I V, F) within a α-helical domain of a native membrane protein are replaced with hydrophilic, non-ionic amino acid residues (Q, T, T, Y, respectively, or "Q, T, Y") and/or N and S. The invention also encompasses a method of preparing a water-soluble polypeptide comprising replacing a plurality of hydrophobic amino acid residues (L, I V, F) within the α-helical domain(s) of a native membrane protein with hydrophilic, non-ionic amino acid residues (Q, T, Y). The invention additionally encompasses a polypeptide prepared by replacing a plurality of hydrophobic amino acid residues (L, I V, F) within the α-helical domain of a native membrane protein with hydrophilic, non-ionic amino acid residues (Q, T, Y, respectively). The variant can be characterized by the name of the parent or native protein (e.g., CXCR2) followed by the abbreviation "QTY" (e.g., CXCR2-QTY).

The present invention is directed to a method of designing, selecting and/or producing Fc fusion QTY GCPR proteins, these proteins produced by the process, compositions comprising said polypeptides, and methods of use thereof. In particular, the method relates to a process for designing proteins using the "QTY code Principle," changing the water-insoluble amino acids (Leu, Ile, Val and Phe, or the single letter code L, I, V, F) into water-soluble, non-ionic amino acids (Gln, Thr and Tyr, or the single letter code Q, T, Y). Furthermore, two additional non-ionic amino acids Asn (N) and Ser (S) may also be used for the substitution for L, I and V but not for F. In the embodiments discussed below, it is to be understood that Asn (N) and Ser (S) are envisioned as being substitutable for Q and T (as a variant is described) or L, I or V (as a native protein is described). For the purposes of brevity, however, the application does not explicitly state these alternative embodiments.

The invention utilizes a modified, synthetic, and/or non-naturally occurring, α-helical domain(s) and water-soluble polypeptides mimicking transmembrane regions (e.g., "sTMs" or "QTY TMs") comprising such modified α-helical domain(s), wherein the modified α-helical domain(s) comprise an amino acid sequence in which a plurality of hydrophobic amino acid residues (L, I V, F) within a α-helical domain of a native membrane protein are replaced with hydrophilic, non-ionic amino acid residues (Q, T, T, Y, respectively, or "Q, T, Y") and/or N and S. The invention also encompasses a method of preparing a water-soluble polypeptide comprising replacing a plurality of hydrophobic amino acid residues (L, I V, F) within the α-helical domain(s) of a native membrane protein with hydrophilic, non-ionic amino acid residues (Q, T, Y). The invention additionally encompasses a polypeptide prepared by replacing a plurality of hydrophobic amino acid residues (L, I V, F) within the α-helical domain of a native membrane protein with hydrophilic, non-ionic amino acid residues (Q, T, Y., respectively). The variant can be characterized by the name of the parent or native protein (e.g., the CCR) preceded or followed by the abbreviation "QTY" (e.g., QTY CCR9, CCR9 QTY or CCR9$^{QTY}$).

In yet an additional embodiment, the native membrane protein or membrane protein is an integral membrane protein. In a further aspect, the native membrane protein is a mammalian protein. The proteins of the invention are preferably human. For the purposes of being concise, references to specific GPCR proteins (e.g., CXCR2) are intended to refer to both mammalian, generally, and, in the alternative, human, specifically. In other embodiments, the α-helical domain is one of 7-transmembrane α-helical domains in a G-protein coupled receptor (GPCR) variant modified, for example, in the extracellular or intracellular loops to improve or alter ligand binding, as described elsewhere in the literature. For the purposes of this invention, the word "native" is intended to refer to the protein (or α-helical domain) prior to water solubilization in accordance with the methods described herein.

GPCRs typically have 7-transmembrane alpha-helices (7TM) and 8 non-TM. These transmembrane segments are called TM1, TM2, TM3, TM4, TM5, TM6 and TM7. The 8 non-transmembrane loops are divided into 4 extracellular loops N-terminus, EC1, EC2, EC3, and 4 intracellular non-TM, IC1, IC2, IC3, C-terminus, thus total 8 non-TMs.

respectively). The sGPCRs of the invention are characterized by water solubility and ligand binding. In particular, the sGPCR binds the same natural ligand as the corresponding native GPCR.

CCR-9 C-C chemokine receptor type 9 isoform B: Replacing all or substantially all of the hydrophobic amino acids, L, I, V, and F, with Q, T and Y (respectively) within the transmembrane domains results in the following sequence (lower line SEQ ID NO: 1), aligned with the wild type (top line SEQ ID NO: 2):

```
  1  MTPTDFTSPIPNMADDYGSESTSSMEDYVNFNFTDFYCEKNNVRQFASHFLPPLYWLVFI
     |||||||||||||||||||||||||||||||||||||||||||||||||..||.||....
     MTPTDFTSPIPNMADDYGSESTSSMEDYVNFNFTDFYCEKNNVRQFASHYQPPQYWQTYT

61  VGALGNSLVILVYWYCTRVKTMTDMFLLNLAIADLLFLVTLPFWAIAAADQWKFQTFMCK
     .||.|||.....|||||||||||||...|.|.||.....|.|.||.||||||||||||||
     TGAQGNSQTTQTYWYCTRVKTMTDMYQQNQATADQQYQTTQPYWATAAADQWKFQTFMCK

121  VVNSMYKMNFYSCVLLIMCISVDRYIAIAQAMRAHTWREKRLLYSKMVCFTIWVLAAALC
     ..|||||||.|||....||.|.|||.|.|||||||||||||..||||.|.|.|..|||.|
     TTNSMYKMNYYSCTQQTMCTSTDRYTATAQAMRAHTWREKRQQYSKMTCYTTWTQAAAQC

181  IPEILYSQIKEESGIAICTMVYPSDESTKLKSAVLTLKVILGFFLPFVVMACCYTIIIHT
     .||..||||||||||||||||||||||||.|||..|.|...|...|...||||||...||
     TPETQYSQIKEESGIAICTMVYPSDESTKQKSATQTQKTTQGYYQPYTTMACCYTTTTHT

241  LIQAKKSSKHKALKVTITVLTVFVLSQFPYNCILLVQTIDAYAMFISNCAVSTNIDICFQ
     ..||||||||||.|.|.|.||....||.||||....||.|||||||||||.|||.|.|.|
     QTQAKKSSKHKAQKTTTTTQTTYTQSQYPYNCTQQTQTTDAYAMFISNCATSTNTDTCYQ

301  VTQTIAFFHSCLNPVLYVFVGERFRRDLVKTLKNLGCISQAQWVSFTRREGSLKLSSMLL
     .|||.|..|||.||..|...||||||||||||||||||||||||||||||||||||||||
     TTQTTAYYHSCQNPTQYTYTGERFRRDLVKTLKNLGCISQAQWVSFTRREGSLKLSSMLL

361  ETTSGALSL
     |||||||||
     ETTSGALSL
```

We can therefore divide a GPCR protein into 15 fragments based on the transmembrane and non-transmembrane features.

The hydrophilic residues (which replace one or more hydrophobic residues in the α-helical domain of a native membrane protein) are selected from the group consisting of glutamine (Q), threonine (T), tyrosine (Y) and any combination thereof. In additional aspects, the hydrophobic residues selected from leucine (L), isoleucine (I), valine (V) and phenylalanine (F) are replaced. Specifically, the phenylalanine residues of the α-helical domain of the protein are replaced with tyrosine; the isoleucine and/or valine residues of the α-helical domain of the protein are replaced with threonine; and/or the leucine residues of the α-helical domain of the protein are replaced with glutamine.

The invention contemplates water soluble GPCR variants ("sGPCRs") characterized by a plurality of transmembrane domains independently characterized by at least 50%, preferably at least about 60%, more preferably at least about 70% or 80%, such as at least about 90%) of the hydrophobic amino acid residues (I/L, V and F) of a native transmembrane protein (e.g., GPCR) substituted by a T, Q or Y, Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V, and F amino acids, as set forth in the wild type sequence.

Coding sequences can be designed, shuffled and proteins expressed. The expressed proteins can be assayed for ligand binding, as described herein.

CXCR2 chemokine receptor type 2: Replacing all or substantially all of the hydrophobic amino acids, L, I V, and F, with Q, T and Y (respectively) within the transmembrane domains results in the following sequence (lower line SEQ ID NO: 3), aligned with the wild type (top line SEQ ID NO: 4):

```
  1  MTPTDFTSPIPNMADDYGSESTSSMEDYVNFNFTDFYCEKNNVRQFASHFLPPLYWLVFI
     |||||||||||||||||||||||||||||||||||||||||||||||||..||.||....
     MTPTDFTSPIPNMADDYGSESTSSMEDYVNFNFTDFYCEKNNVRQFASHYQPPQYWQTYT

61  VGALGNSLVILVYWYCTRVKTMTDMFLLNLAIADLLFLVTLPFWAIAAADQWKFQTFMCK
     .||.|||.....|||||||||||||...|.|.||.....|.|.||.||||||||||||||
     TGAQGNSQTTQTYWYCTRVKTMTDMYQQNQATADQQYQTTQPYWATAAADQWKFQTFMCK
```

-continued

```
121  VVNSMYKMNFYSCVLLIMCISVDRYIAIAQAMRAHTWREKRLLYSKMVCFTIWVLAAALC
     ..||||||.|||....||.|.|||.|.||||||||||||.||||.|.|.|..|||.|
     TTNSMYKMNYYSCTQQTMCTSTDRYTATAQAMRAHTWREKRQQYSKMTCYTTWTQAAAQC

181  IPEILYSQIKEESGIAICTMVYPSDESTKLKSAVLTLKVILGFFLPFVVMACCYTIIIHT
     .||..||||||||||||||||||||||||.|||..|.|...|...|...||||||...||
     TPETQYSQIKEESGIAICTMVYPSDESTKQKSATQTQKTTQGYYQPYTTMACCYTTTTHT

241  LIQAKKSSKHKALKVTITVLTVFVLSQFPYNCILLVQTIDAYAMFISNCAVSTNIDICFQ
     ..||||||||||.|.|.|..|....||.||||....||.||||||||||.|||.|.|.|
     QTQAKKSSKHKAQKTTTTQTTYTQSQYPYNCTQQTQTTDAYAMFISNCATSTNTDTCYQ

301  VTQTIAFFHSCLNPVLYVFVGERFRRDLVKTLKNLGCISQAQWVSFTRREGSLKLSSMLL
     .|||.|..|||.||..|...|||||||||||||||||||||||||||||||||||||||
     TTQTTAYYHSCQNPTQYTYTGERFRRDLVKTLKNLGCISQAQWVSFTRREGSLKLSSMLL

361  ETTSGALSL
     |||||||||
     ETTSGALSL
```

Each of the predicted transmembrane regions has been underlined and exemplified a fully modified domain of the invention. Thus, for example, the invention includes a transmembrane domain comprising each underlined domain. Preferably the protein comprising TM1 herein includes one or more (e.g., all) of the extracellular and intracellular loop sequences (the sequences which have not been underlined). In addition or alternatively, the protein comprising the TM1 herein includes one or more additional transmembrane regions (the underlined sequences) in the depicted protein or homologous sequences retaining one, two, three or, possibly four or more of the native L, I V and F amino acids, as set forth in the wild type sequence.

Coding sequences can be designed, shuffled and proteins expressed. The expressed proteins can be assayed for ligand binding, as described herein.

Each QTY TM Domain can be a complete transmembrane domain or a portion thereof. For example, the QTY TM Domain can be the first 1, 2, 3, 4, or more helical turns (approximately 4 amino acids per helical turn) from the extracellular surface of the transmembrane region. Additionally, amino acids that are proximal and/or external to the transmembrane region can be included. For example, the native amino acids of the parent protein that are 1, 2, 3, 4, or 5 amino acids upstream and/or downstream of the transmembrane region can be included in the QTY TM Domain. Optimizing the amino acids that couple or fuse the ligand binding domain to the QTY TM Domain can control the presentation of the ligand binding domain faces to the desired ligand. For example, where ligand binding domains (e.g., an alpha and beta subunit) are oriented to present an inward face (the surface of a first ligand binding domain that is proximal to the surface of a second ligand binding domain) which increases affinity or specificity for a ligand, amino acids coupling the ligand binding domain to the QTY TM domain can preserve the three-dimensional presentation of the ligand binding domain(s).

The QTY TM Domain can include one or more amino acid variants that present an additional reactive moiety for functionalization. For example, a hydroxyl, carboxyl or amino group on an amino acid side chain can be further functionalized, for example with a polyethylene glycol or carbohydrate. Further functionalization can improve serum half-life of the Fc fusion receptor protein.

The ligand binding or extracellular domains of the GPCRs can be a native or wild type protein or naturally occurring alleles and splice variants, such as the extracellular domains of the receptors described herein. Where two or more ligand binding domains are required for binding, or selective binding, to the desirable ligand, that the natively outward faces of the ligand binding domains be preserved in selecting the linker moieties.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt alpha-helices.

As used herein, "non-conservative substitutions" are defined as exchanges of an amino acid by another amino acid listed in a different group of the six standard amino acid groups (1) to (6) shown above. QTY substitutions are clearly "non-conservative substitutions", the substitutions are from hydrophobic to hydrophilic without introducing any charges.

In various embodiments, the substitutions may also include non-classical amino acids (e.g., selenocysteine, pyrrolysine, N-formylmethionine .beta.-alanine, GABA and delta-Aminolevulinic acid, 4-aminobenzoic acid (PABA), D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, beta-alanine, fluoro-amino acids, designer amino acids such as beta methyl amino acids, C alpha-methyl amino acids, N alpha-methyl amino acids, and amino acid analogs in general).

Mutations may also be made to the nucleotide sequences of the heterodimeric proteins by reference to the genetic code, including taking into account codon degeneracy.

In various embodiments, the present heterodimeric proteins may comprises variants of any of the known extracellular domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences. In embodiments, a ligand binding domain can differ from a wild type sequence, or parent protein, by 1, 2, 3, 4, 5, 6, 7, 8, 9, 10 or more amino acid substitutions.

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. and has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Fc Domain

The Fc domain of the fusion protein comprises at least a portion of a constant immunoglobulin domain, e.g., a constant heavy immunoglobulin domain or a constant light immunoglobulin domain. Preferably, the second domain comprises at least a portion of a constant heavy immunoglobulin domain. The constant heavy immunoglobulin domain is preferably an Fc fragment comprising the CH2 and CH3 domain and, optionally, at least a part of the hinge region. The immunoglobulin domain may be an IgG, IgD, IgE, IgA, or IgM, immunoglobulin domain or a modified immunoglobulin domain derived therefrom. Preferably, the second domain comprises at least a portion of a constant IgG immunoglobulin domain. The IgG immunoglobulin domain may be selected from IgG1, IgG2, IgG3 of IgG4 domains or from modified domains such as are described in U.S. Pat. No. 5,925,734.

The Fc Domain is preferably a mammalian sequence, more preferably a human sequence, or a variant of a human sequence. The examples provided below illustrate a murine IgG2 Fc domain for study purposes.

Fc domain variants have been described. For example, the Fc domain can contain one or more amino acid substitutions at amino acid residue 250, 252, 254, 256, 308, 309, 311, 428, 433 or 434 (in accordance with Kabat numbering), or equivalents thereof. For example, the amino acid substitution at amino acid residue 250 is a substitution with glutamine; the amino acid substitution at amino acid residue 252 is a substitution with tyrosine, phenylalanine, tryptophan or threonine; the amino acid substitution at amino acid residue 254 is a substitution with threonine; the amino acid substitution at amino acid residue 256 is a substitution with serine, arginine, glutamine, glutamic acid, aspartic acid, or threonine; the amino acid substitution at amino acid residue 308 is a substitution with threonine; the amino acid substitution at amino acid residue 309 is a substitution with proline; the amino acid substitution at amino acid residue 311 is a substitution with serine; the amino acid substitution at amino acid residue 385 is a substitution with arginine, aspartic acid, serine, threonine, histidine, lysine, alanine or glycine; the amino acid substitution at amino acid residue 386 is a substitution with threonine, proline, aspartic acid, serine, lysine, arginine, isoleucine, or methionine; the amino acid substitution at amino acid residue 387 is a substitution with arginine, proline, histidine, serine, threonine, or alanine; the amino acid substitution at amino acid residue 389 is a substitution with proline, serine or asparagine; the amino acid substitution at amino acid residue 428 is a substitution with leucine; the amino acid substitution at amino acid residue 433 is a substitution with arginine, serine, isoleucine, proline, or glutamine; and the amino acid substitution at amino acid residue 434 is a substitution with histidine, phenylalanine, or tyrosine.

In some embodiments, the Fc domain (e.g., comprising an IgG constant region) comprises one or more mutations such as substitutions at amino acid residue 252, 254, 256, 433, 434, or 436 (in accordance with Kabat numbering). For example, the IgG constant region includes a triple M252Y/S254T/T256E mutation or YTE mutation; the IgG constant region includes a triple H433K/N434F/N436H mutation or KFH mutation; or the IgG constant region includes an YTE and KFH mutation in combination.

In some embodiments, illustrative mutations include T250Q, M428L, T307A, E380A, I253A, H310A, M428L, H433K, N434A, N434F, N434S, and H435A and combinations thereof. Additional exemplary mutations in the IgG constant region are described, for example, in Robbie, et al., Antimicrobial Agents and Chemotherapy (2013), 57(12):

6147-6153, Dall'Acqua et al., JBC (2006), 281(33):23514-24, Dall'Acqua et al., Journal of Immunology (2002), 169: 5171-80, Ko et al. Nature (2014) 514:642-645, Grevys et al. Journal of Immunology. (2015), 194(11):5497-508, and U.S. Pat. No. 7,083,784.

The immunoglobulin domain may exhibit effector functions, particularly effector functions selected from ADCC and/or CDC. In some embodiments, however, modified immunoglobulin domains having modified, e.g., at least partially deleted, effector functions can be used.

The Fc Domain can be modified. For example, glycosylation variants can improve or serum half. Enhanced Fc fusion protein comprising an immunoglobulin Fc region or domain comprising at least one oligosaccharide can be produced by exposing the Fc fusion protein to at least one glycosyltransferase. Pegylating the Fc domain can also improve the serum half-life.

The Fc Domain can be linked to the QTY GPCR with a hinge region, derived from an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge regions are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In other embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites.

In various embodiments, the Fc Domain may comprises variants of known domains, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequences. In embodiments, the Fc Domain can differ from a wild type sequence, or parent protein, by 1, 2, 3, 4, 5, 6, 7, 8, 9, 10 or more amino acid substitutions.

Fc QTY GPCR Proteins

Typically, QTY GPCR domain can be directly or indirectly bound to the Fc Domain via an intracellular region (either the N terminal or C terminal) of the QTY GPCR. Additionally or alternatively, flexible simple amino acid linkers (e.g., polyglycine linkers) or rigid linkers (e.g., alpha helical domain, such as a QTY TM domain), can be used.

Vectors & Polynucleotides

In other embodiments, the application provides nucleic acids encoding any of the various Fc fusion proteins disclosed herein. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA, 100(2):438-442 (Jan. 21, 2003); Sinclair et al., Protein Expr. Purif, 26(I):96-105 (October 2002); Connell, N. D., Curr. Opin. Biotechnol., 12(5):446-449 (October 2001); Makrides et al., Microbiol Rev., 60(3):512-538 (September 1996); and Sharp et at., Yeast, 7(7):657-678 (October 1991).

General techniques for nucleic acid manipulation are described for example in Sambrook et al., Molecular Cloning: A Laboratory Manual, 2nd Edition, Vols. 1-3, Cold Spring Harbor Laboratory Press (1989), or Ausubel, F. et at., Current Protocols in Molecular Biology, Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The Fc fusion receptor proteins may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An N-terminal leader sequence can be removed by the host cell following expression.

For prokaryotic host cells that do not recognize and process a native signal sequence, the signal sequence is substituted by a prokaryotic signal sequence selected, for example, from the group of the alkaline phosphatase, penicillinase, 1pp, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria, yeast, and viruses. The origin of replication from the plasmid pBR322 is suitable for most Gram-negative bacteria, the 2-micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein disclosed herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein disclosed herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tall to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins disclosed herein by higher eukaryotes is often increased by inserting an enhancer sequence into the vector. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein disclosed herein. One useful transcription termination component is the bovine growth hormone polyadenylation region. See WO94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, Rho tag, Strep tag or a GST tag. Appropriate cloning and expression vectors for use with bacterial, fungal, yeast, and mammalian cellular hosts can be found in Cloning Vectors: A Laboratory Manual, (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram-positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (Bio/Technology, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Receptor Protein Production

Host cells containing vectors encoding the Fc fusion receptor proteins described herein, as well as methods for producing the Fc fusion receptor proteins are described herein. Host cells may be transformed with the herein-described expression or cloning vectors for protein production and cultured in conventional nutrient media modified as appropriate for inducing promoters, selecting transformants, or amplifying the genes encoding the desired sequences. Host cells useful for high-throughput protein production (HTPP) and mid-scale production include the HMS174-bacterial strain. The host cells used to produce the proteins disclosed herein may be cultured in a variety of media. Commercially available media such as Ham's F10 (Sigma), Minimal Essential Medium ((MEM), (Sigma)), RPM1-1640 (Sigma), and Dulbecco's Modified Eagle's Medium ((DMEM), Sigma)) are suitable for culturing the host cells. In addition, many of the media described in Ham et al., Meth. Enzymol., 58:44 (1979), Barites et al., Anal. Biochem., 102:255 (1980), U.S. Pat. Nos. 4,767,704, 4,657,866, 4,927,762, 4,560,655, 5,122,469, 6,048,728, 5,672,502, or U.S. Pat. No. RE 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression and will be apparent to the ordinarily skilled artisan.

The Fc fusion receptor proteins provided herein can also be produced using cell-free translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial ceil-free translation system.

The Fc fusion receptor proteins disclosed herein can also be produced by chemical synthesis (e.g., by the methods described in Solid Phase Peptide Synthesis, 2nd Edition, The Pierce Chemical Co., Rockford, Ill. (1984)). Modifications to the Fc fusion receptor proteins can also be produced by chemical synthesis.

The Fc fusion receptor proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, counter-currant distribution or any combinations of these. After purification, polypeptides may be exchanged into different buffers and/or concentrated by any of a variety of methods known to the art, including, but not limited to, filtration and dialysis.

The purified Fc fusion proteins are preferably at least 85% pure, or preferably at least 95% pure, and most preferably at least 98% pure. Regardless of the exact numerical value of the purity, the Fc fusion protein is sufficiently pure for use as a pharmaceutical product.

QTY Design

In some aspects, the invention is directed to the use of the QTY (Glutamine, threonine and tyrosine) replacement (or "Code") method (or "principle") to change the transmembrane α-helix hydrophobic residues leucine (L), isoleucine (I), valine (V), and phenylalanine (F) of a native protein to the hydrophilic residues glutamine (Q), threonine (T) and tyrosine (Y), or alternatively, as described above, Asn (N) and Ser (S) for L, I and/or V. This invention can convert a water insoluble, native membrane protein to a water-soluble counterpart.

The applicants specifically designed the QTY receptor variants to fuse with the Fc region of IgG protein in order to acquire an antibody-like structure, as well as to promote their antibody-like functions and properties for specific ligand recognition and binding while retaining their receptor characteristics. A spacer was introduced to optimize the conformation of QTY code designed receptors in the heavy chain. We used the Fc region of mouse IgG2a in the specific design as it is the functional equivalent of human IgG1. Mouse IgG is chosen over human IgG due to the consideration of implementing mouse cytokine storm model in subsequent experiments, which is beyond the scope of current study. The Fc region can be easily exchanged in future designs. The structural illustrations were obtained through Uniprot where applicable or from a homology model (CXCR2) (Kwon, 2010).

Bioinformatics Analysis

QTY variant protein sequences were analyzed using a web-based tool TMHMM Server v2.0 to predict the existence of hydrophobic transmembrane segments. The server is based on a Hidden Markov Model (HMM) that takes into account actual biological architectures of a transmembrane helix whereas likelihood of presence is calculated (Sonnhammer et al., 1998).

Protein hydrophobicity can be plotted versus the protein sequences. The X-axis can show the number of amino acids in sequences from N-terminus to C-terminus. In interleukin and interferon receptors, a single high probability hydrophobic segment near the C-terminus end of each receptor and are also eliminated though QTY modification. The hydrophobicity of both extracellular and intracellular components is unchanged. E. coli expression and gel-electrophoresis of QTY variant receptors. The corresponding genes with E. coli specific codons were synthesized and expressed in sufficient quantities. The throughput for each receptor differed but was all in mg/L range in LB media. All Fc fusion receptors were expressed into inclusion bodies. They were purified by a) affinity purification, and b) gel filtration in denatured state and then folded into functional state for subsequent analysis. Both arginine and DTT were beneficial for solubilizing the proteins so either or both of them were included in the storage buffer or for ligand binding tests.

Bold denotes transmembrane region of a receptor, within which, QTY substitution has occurred. Underlined parts are tags and restriction sites used for purification and future swapping of the Fc region for tests in respective animals. Italicized sequence corresponds to the Fc region of IgG protein, where in this case, is mouse IgG2a-Fc, the functional equivalent of human IgG1. The hinge region has the sequence PRGPTIKPCPPCKCPAPNLLGGP (SEQ ID NO. 5), following the underlined sequences.

CCR9-QTY Fc
(SEQ ID NO. 6)
MTPTDFTSPIPNMADDYGSESTSSMEDYVNFNFTDFYCEKNNVRQFASH

YQPPQYWQTYTTGAQGNSQTTQTYWYCTRVKTMTDMYQQNQATADQQYQ

TTQPYWATAAADQWKFQTFMCKTTNSMYKMNYYSCTQQTMCTSTDRYTA

TAQAMRAHTWREKRQQYSKMTCYTTWTQAAAQCTPETQYSQIKEESGIA

ICTMVYPSDESTKQKSATQTQKTTQGYYQPYTTMACCYTTTTHTQTQAK

KSSKHKAQKTTTTTQTTYTQSQYPYNCTQQTQTTDAYAMFISNCATSTN

TDTCYQTTQTTAYYHSCQNPTQYTYTGERFRRDLVKTLKNLGCISQAQW

VSFTRREGSLKLSSMLLETTSGALSLTETSQVAPAHHHHHHHHH<u>TETS</u>

<u>QVAPAHHHHHHHHHGSKLVD</u> *PRGPTIKPCPPCKCPAPNLLGGPSVFIF*

*PPKIKDVLMISLSPIVTCVVVDVSEDDPDVQISWFVNNVEVHTAQTQTH*

*REDYNSTLRVVSALPIQHQDWMSGKEFKCKVNNKDLPAPIERTISKPKG*

*SVRAPQVYVLPPPEEEMTKKQVTLTCMVTDFMPEDIYVEWTNNGKTELN*

*YKNTEPVLDSDGSYFMYSKLRVEKKNWVERNSYSCSVVHEGLHNHHTTK*

*SFSRTPGK*

CXCR2-QTY Fc:
(SEQ ID NO. 7)
MEDFNMESDSFEDFWKGEDLSNYSYSSTLPPFLLDAAPCEPESLEINKY

YTTTTYAQTYQQSQQGNSQTMQTTQYSRVGRSVTDTYQQNQAQADQQYA

QTQPTWAASKVNGWIFGTFLCKTTSQQKETNYYSGTQQQACTSTDRYLA

IVHATRTLTQKRYLVKYTCQSTWGQSQQQAQPTQQYRRTVYSSNVSPAC

YEDMGNNTANWRMQQRTQPQSYGYTQPQQTMQYCYGFTLRTLFKAHMGQ

-continued
KHRAMRTTYATTQTYQQCWQPYNQTQQADTLMRTQVIQETCERRNHIDR

AQDATETQGTQHSCQNPQTYAYTGQKFRHGLLKILAIHGLISKDSLPKD

SRPSFVGSSSGHTSTTL<u>TETSQVAPAHHHHHHHHHGSKLVD</u>*PRGPTIK*

*PCPPCKCPAPNLLGGPSVFIFPPKIKDVLMISLSPIVTCVVVDVSEDDP*

*DVQISWFVNNVEVHTAQTQTHREDYNSTLRVVSALPIQHQDWMSGKEFK*

*CKVNNKDLPAPIERTISKPKGSVRAPQVYVLPPPEEEMTKKQVTLTCMV*

*TDFMPEDIYVEWTNNGKTELNYKNTEPVLDSDGSYFMYSKLRVEKKNWV*

*ERNSYSCSVVHEGLHNHHTTKSFSRTPGK*

Ligand-Binding Measurement in Buffer

The affinity of QTY modified cytokine receptor fused with Fc of IgG for their respective native ligands was measured using MicroScale Thermophoresis (MST). Changes in thermophoretic movement for labeled proteins upon ligand-binding were recorded and plotted as a function of ligand concentration. Both QTY code designed Fc-fusion interleukin and interferon receptors showed no non-specific adhesion or aggregation during the measurement.

QTY Fc-fusion receptors exhibit affinity for their respective ligands typically in nM to tens of nM range (Table 1). The affinities are lower compared to the native receptors without Fc-fusion. For affinities of interleukin and interferon receptors, previous reported studies primarily used human neutrophils cell-based assay with isotope $^{125}$I-labeled ligand that is significantly more sensitive than using the purified receptors measured by biophysical instrument, thus they may not be directly comparable. The affinity $K_d$ derived from MST displays similar values compared to previous SPR measurement on purified proteins with the exception of IL4R$^{QTY}$-Fc. The method that was used to determine the $K_d$ in literature was also included in the Table.

TABLE

Ligand-binding affinity of Fc fused QTY cytokine receptors

| | Native ($K_d$, nM) | QTY variant ($K_d$, nM) |
|---|---|---|
| CCR9$^{QTY}$-Fc vs CCL25 | ~8 (Eberhardson et al., 2017) | 37.2 ± 15.7 |
| CXCR2$^{QTY}$-Fc vs IL8 | 0.5 ± 0.3 (Monomer) 8.5 ± 2.0 (Dimer) (Rajarathnam et al., 2006) | 60.3 ± 21.0 |

The applicants' Fc-fusion water-soluble receptors, as a decoy, can rapidly soak up excessive cytokines during "cytokine storm" unleashed during CAR-T treatment and COVID-19. When the designed water-soluble Fc-receptors bind to excessive cytokines, they act as decoy to prevent the excessive cytokine to directly interact with target cells, therefore reducing the organ damage and toxicity conferred by "cytokine storm". There are over 20 Fc-fusion proteins commercially available and several of these have been developed as therapeutics (Czajkowsky et al., 2012). Although there have been many Fc-fusion proteins developed for various applications, they are water-soluble proteins (Czajkowsky et al., 2012; Mekhaiel et al., 2011). The applicants' QTY code designed Fc-fusion receptors provide a novel platform for further design of other types of fusion membrane receptors for therapeutic and diagnostic applications.

The design and synthesis of functionally equivalent transmembrane proteins have implications beyond biological and clinical use. Highly specific towards their respective ligands, QTY code modified transmembrane proteins can also serve as ideal candidates for molecular sensing. Complex electrical arrays functionalized with a variety types of water-soluble membrane proteins can potentially mimic cell response in vitro and be fabricated into a pseudo cell with electrical readouts.

Thus, one or more Fc-fusion proteins of the invention can be administered to a patient in need thereof, (e.g., to treat cytokine storm) in a therapeutically effective amount to bind one or more cognate cytokines. In addition, one or more Fc-fusion proteins of the invention can be contacted with blood, e.g., extracorporeally, to a patient in need thereof, (e.g., to treat cytokine storm) in a therapeutically effective amount to bind one or more cognate cytokines.

Typically, extracorporeal treatment to remove cytokines from a patient's blood stream will benefit from immobilizing the Fc fusion protein(s) of the invention. Thus, the invention includes a sorbent material having a substrate (e.g., polymer beads, glass beads, magnetic beads, porous polymers, membranes) upon which an Fc fusion protein of the invention is immobilized. Immobilization can be accomplished by covalent or non-covalent binding. The sorbent material can be loaded into a cartridge. The sorbent material of the invention can also be used in diagnostics to screen and identify the presence (and/or quantity) of one or more cytokines.

The Fc fusion proteins can be directly or indirectly bound to a substrate or absorbent material. Binding with a so-called S-layer allows directed patterned binding. Binding without an S-layer can occur in a random oriented fashion, leading to a less dense distribution on the surface and the potential for "empty spaces" on the support. Non-specific adsorption of serum components may occur with random distribution. A functional S-layer lattice can be stabilized both by inter- and intramolecular cross-linking within the protein lattice and by introducing (cross)linkers between the S-layer and the supporting layer. Such structures reveal a considerable higher chemical and mechanical stability compared to functional layers composed of randomly bound molecules which are only cross linked to the supporting layer. Support-structures (beads, plane surfaces, gels) functionalized with Protein A can be a useful starting material for generating products of the invention. Such matrices could be used for direct binding the antibody-like receptor molecules. Nevertheless, such composites will be less stable and reveal more leakage than S-layer based material even after crosslinking. It is anticipated that such materials are suitable for the first in vitro studies using cytokine spiked plasma.

In one embodiment, a substrate comprising self-assembled Fc fusion proteins of the invention, as generally described in WO 2019/046699, which is incorporated herein by reference. Specifically, the N-terminus of the S-layer fusion protein binds to the solid substrate or support. Thus, the self-assembling unit bound to the surface of the substrate can comprise elements arranged as follows:

Substrate Surface—[N-S-layer protein-C-Fusion Domain]—[(Binding Moiety-C-QTY N];

wherein "N" and "C" indicate the N and C-termini, respectively, and wherein - represents covalent or non-covalent, direct or indirect, attachment of the S-layer fusion protein to the substrate surface and binding of the fusion domain of the S-layer fusion protein to the binding moiety of the fusion protein.

Substrates include organic and inorganic, hydrophobic or hydrophilic materials, such as polystyrene surfaces, silicon wafers (SiO2, Si3N4, hydrophilic, and/or hydrophobic), gold wafers, glass, metal oxide surfaces (for example, aluminum oxide, indium tin oxide), stainless steel, modified graphene, carbon nanotubes, poly-lysine modified surfaces, magnetic beads, ELISA plates, silica beads, filling materials for column chromatography, coating resins for blood purification, and polyamide membranes. For example, the surface can be a semi-conducting or conducting surface, including, but not limited to, silicon, gold, conducting polymers, carbon nanotubes, and graphene. For example, the surface protein can recrystallize on a silicon wafer, a silicon dioxide-coated silicon wafer, indium tin oxide (ITO) coated glass, or $TiO_2$—$SiO_2$ hybrid sol-gel coated glass. In an additional example, the substrate can be surface-treated with poly-l-lysine, for example, poly-l-lysine-treated gold. In certain additional aspects, the substrate can be flexible plastic, for example, ITO coated plastic film, graphene coated film, or $TiO_2$—$SiO_2$ hybrid sol-gel coated film. In certain additional aspects, the solid support is a sensor chip of a surface plasmon resonance system.

The surface preferably comprises a high density of proteins, such as between about 2.37 to about $4.37 \times 10^{12}$ per 1 $cm^2$. In certain embodiments, at least two, three, four, five or more different cytokine receptor variants can be immobilized on the substrate. For example, at least two different receptor variants (for example, CXCR2 and CCR9 variants) can be immobilized on the surface.

The proteins can preferably crosslinked, thereby improving stability on the surface. Examples include dimethyl pimelimidate, glutaraldehyde, bis(sulfosuccinimidyl)superat, amino-carboxyl group directed crosslinkers including, for example, 1-ethyl-3-(3-dimethylaminopropyl)carbodiimide and other amine-amino directed linkers. Cross linked S-layer lattices can avoid leakage, which is preferred for extracorporeal blood purification.

Substrates with immobilized Fc fusion proteins can be loaded into cartridges, which may be arranged in series or in parallel. In such arrangements more than one type of adsorbent (e.g., each with a different cytokine receptor) may be linked to the blood stream simultaneously. The progress of cytokine removal during the procedure (concentration of cytokines in the plasma) can be simultaneously monitored and rapidly stopped if the desired concentration is achieved. Time-controlled procedures can offer a great advantage in case of emergency treatment.

COVID-19 infection can be associated with severe Thrombosis. The cause for this side effect of the viral infection is obviously not yet understood. In comparison to treatments involving injection of water-soluble cytokine receptors, risk for Thrombosis can be mitigated with extracorporeal therapy. Extracorporeal sorbents (Apheresis procedures) may benefit from a faster approval process.

A potential application for extracorporeal purification can be detoxification. QTY GPCR proteins with high binding capacities for specific drugs can have a great potential to remove the components (drugs) from the blood stream. This could open a field and stimulate the screening for new "binding sites" (drug/protein interaction).

The invention contemplates a process for direct binding of the water soluble (QTY code modified) GPCR proteins and derived antibody-like receptor molecules for sorbent technologies for cytokine removal in human septic shock and for producing matrices for diagnostic tools (e.g., solid phase immunoassays, ELISA, QCMD).

In addition, the sorbent can be used in the purification of the cytokines and/or chemokines, such as from cell culture supernatants. For example, the sorbent can be used in chromatography column. Cross-linking the protein matrices as described above can be beneficial. The cytokines and/or chemokines can be removed from the sorbent according to known techniques. Sorbents utilizing magnetic beads can facilitate isolation and recovery. The sorbents of the invention can reduce production costs.

Materials and Methods

Genes Identification and QTY Modification

Sequences of the respective proteins were obtained from Uniprot: www.uniprot.org/. Respective extracellular, transmembrane and cytoplasmic domains were identified. QTY code was only applied to the transmembrane helical domain to solubilize the proteins.

Bioinformatics Analysis

Protein properties were calculated based on their primary sequences via the open access web-based tool ExPASy: https://web.expasy.org/protparam/. The existence of hydrophobic patch within the transmembrane region in native and QTY variant protein sequences was determined via the open access web-based tool TMHMM Server v.2.0: www.cbs.dtu.dk/services/TMHMM-2.0.

E. coli Expression System and Protein Purification

Genes of QTY modified cytokine receptor proteins were cloned into Fc region of mouse IgG2a which is the functional equivalence of human IgG1. The full sequences were codon optimized for E. coli expression and obtained from Genscript. The genes were cloned into pET20b expression vector with Carbenicillin resistance. The plasmids were reconstituted and transformed into E. coli BL21(DE3) strain. Transformants were selected on LB medium plates with 100 µg/ml Carbenicillin. E. coli cultures were grown at 37° C. until the $OD_{600}$ reached 0.4-0.8, after which IPTG (isopropyl-D-thiogalactoside) was added to a final concentration of 1 mM followed by 4-hour expression. Cells were lysed by sonication in B-PER™ protein extraction agent (Thermos-Fisher) and centrifuged (23,000×g, 40 min, 4° C.) to collect the inclusion body. The biomass was then subsequently washed twice in buffer 1 (50 mM Tris.HCl pH7.4, 50 mM NaCl, 10 mM CaCl2, 0.1% v/v Trition X100, 2M Urea, 0.2 µm filtered), once in buffer 2 (50 mM Tris.HCl pH7.4, 1M NaCl, 10 mM CaCl2, 0.1% v/v Trition X100, 2M Urea, 0.2 µm filtered) and again in buffer 1. Pellets from each washing step were collected by centrifugation (23,000×g, 25 min, 4° C.).

Washed inclusion bodies were fully solubilized in denaturation buffer (6M guanidine hydrochloride, 1×PBS, 10 mM DTT, 0.2 µm filtered) at room temperature for 1.5 hour with magnetic stirring. The solution was centrifuged at 23,000×g for 40 min at 4° C. The supernatant with proteins was then purified by Qiagen Ni-NTA beads (His-tag) followed by size exclusion chromatography using an ÅKTA Purifier system and a GE healthcare Superdex 200 gel-filtration column. Purified protein was collected and dialyzed twice against renaturation buffer (50 mM Tris. HCl pH 9.0, 3 mM reduced glutathione, 1 mM oxidized glutathione, 5 mM ethylenediaminetetraacetic acid, and 0.5M L-arginine). Following an overnight refolding process, the renatured protein solution was dialyzed into storage buffer of 50 mM Tris. HCl pH 9.0 with various arginine content.

Microscale Thermophoresis

MicroScale Thermophoresis (MST) is an optical method detecting changes in thermophoretic movement and TRIC of the protein-attached fluorophore upon ligand binding. Active labelled proteins contribute to the thermophoresis signal upon ligand binding. Inactive proteins influence the data as background but not the signals and only data from binding proteins are used to derive the $K_d$ value. Herein ligand binding experiments were carried out with 5 nM NT647-labeled protein in 1×PBS, 10 mM DTT buffer with different concentration of arginine, against a gradient of respective ligands on a Monolith NT.115 pico instrument at 25° C. Synthesized receptors were labeled with Monolith NT™ $2^{nd}$ generation protein labeling kit RED-NHS (NanoTemper Technologies) so as to obtain unique fluorescent signals. MST time traces were recorded and analyzed to obtain the highest possible signal-to-noise levels and amplitudes, >5 Fnorm units. The recorded fluorescence was plotted against the concentration of ligand, and curve fitting was performed using the $K_d$ fit formula derived from the law of mass action. For clarity, binding graphs of each independent experiment were normalized to the fraction bound (0=unbound, 1=bound). MST experiments were performed in the Center for Macromolecular Interactions at Harvard Medical School.

$K_d$ Fitting Model:

$K_d$ model is the standard fitting model based on law of mass action.

Curve Fit Formula:

$$F(c_T) = F_u + (F_b - F_u) * \frac{c_{AT}}{c_A}$$

$$\frac{c_{AT}}{c_A} = $$

$$\text{fraction bound} = \frac{1}{2c_A} * \left( c_T + c_A + K_D - \sqrt{(c_T + c_A + K_D)^2 - 4c_T c_A} \right)$$

$F_u$: fluorescence in unbound state
$F_b$: fluorescence in bound state
$K_D$: dissociation constant, to be determined
$c_{AT}$: concentration of formed complex
$C_A$: constant concentration of molecule A (fluorescent), known
$C_T$: concentration of molecule T in serial dilution.

In broad terms, the protein design process comprises all, or substantially all, the steps:
   (1) identifying a first transmembrane region by predicting an alpha-helical structure of a protein;
   (2) modifying a plurality of hydrophobic amino acids via the QTY Code, as defined herein to obtain a modified first transmembrane sequence.

Step-by-Step Description:

1: In step 1, a computer interface of a computer system receives a protein sequence, selected for analysis, and data descriptive of the protein (e.g., the sequence) entered, uploaded or inputted through a computer interface of a computer system. The data entered can be a protein name, a database reference, or a protein sequence. For example, the protein sequence can be uploaded through a computer interface.

2: In step 2, additional data about the protein can be identified, determined, obtained and/or entered, including its name or sequence and entered via the computer interface. One source to obtain protein data is a database named UniProt (www.uniprot.org/). Alternatively, the method of the invention can store data relating to the protein, or related sequences to the protein, for later retrieval by the user in this step. In embodiments, the program can prompt the user to select a database or file for retrieving additional data (e.g., sequence data) relating to the protein selected for analysis.

3: In step 3, the user can enter, upload, or obtain data identifying the transmembrane regions. For example, the user can be prompted to obtain the data from a public source, such as from UniProt. The information can be collected from the database for use in Step 5.

4: Alternatively or additionally, the transmembrane region can be predicted by the method. Transmembrane regions are generally characterized by an alpha helical conformation. Transmembrane helix prediction can be predicted using a software package named TMHMM 2.0 (TransMembrane prediction using Hidden Markov Models), developed by Center for Biological Sequence Analysis. Some versions of the software have some problems on peak finding and sometimes fails to find TM regions. Therefore, in a preferred embodiment, a modified version of the program is used, wherein the peak searching method execute by the computer system introduces a dynamic baseline. Here, if the TMs using the initial baseline value are not found, the baseline can be changed to a lower value. For example, the default baseline is 0.2. One can set the baseline value to 0.1. If too many TMs are found, the baseline can be changed to a higher value, such as 0.15.

5: After identifying the TM data in the form, the sequence of a protein is divided into fragments including transmembrane segments and non-transmembrane segments.

It is understood that the system can execute one or more, such as all of the steps described above, using a computer interface for input by a user.

A first transmembrane region (typically, but not essentially, the transmembrane region which is most proximal to the N-terminal of the protein) is selected for variation. Hydrophobic amino acids (L, I, V, and F) are then substituted with the corresponding hydrophilic amino acid (Q, T or Y). It is understood that the amino acid is not actually substituted into the protein, in this context. Rather, the amino acid designation is substituted in the sequence for modeling. Thus, the term "sequence" is intended to include "sequence data." Typically, most or all of the hydrophobic amino acids are selected for substitution. If less than all amino acids are selected, it may be desirable to select the internal hydrophobic amino acids leaving one or more N and/or C terminal amino acids of the transmembrane regions hydrophobic. Additionally or alternatively, it may be desirable to select to replace all of the leucines (L) in a transmembrane region. Additionally or alternatively, it may be desirable to select to replace all of the isoleucines (I) in a transmembrane region. Additionally or alternatively, it may be desirable to select to replace all of the valines (V) in a transmembrane region. Additionally or alternatively, it may be desirable to select to replace all of the phenylalanines (F) in a transmembrane region. Additionally or alternatively, it can be beneficial to retain one or more phenylalanines in the transmembrane region. Additionally or alternatively, it can be beneficial to retain one or more valines in the transmembrane region. Additionally or alternatively, it can be beneficial to retain one or more leucine in the transmembrane region. Additionally or alternatively, it can be beneficial to retain one or more isoleucines in the transmembrane region. Additionally or alternatively, it can be beneficial to retain one or more hydrophobic amino acids in the transmembrane region where the wild type sequence is characterized by three or more contiguous hydrophobic amino acids. The transmembrane region so designed (the transmembrane variant or "variant") is then subjected to the transmembrane region prediction process, as discussed herein.

The nucleic acid molecules are preferably designed to provide codon optimization and intron deletions for the expression systems selected to produce a library of coding sequences. For example, if the expression system is E. coli, codons optimized for E. coli expression can be selected. www.dna20.com/resources/genedesigner. In addition, a promoter region, such as a promoter suitable for expression in the expression system (e.g., *E. coli*) is selected and operatively connected to the coding sequences in the library of coding sequences.

The initial library of coding sequences, or a portion thereof, is then expressed to produce a library of proteins. The library is then subjected to a ligand binding assay. In the binding assay, fusion proteins are contacted with the ligand, preferably in an aqueous medium and ligand binding is detected.

The invention includes transmembrane domain variants, and nucleic acid molecules encoding same, obtained, or obtainable, from the methods described herein.

The invention further encompasses a method of treatment for a disorder or disease that is mediated by the activity of a membrane protein, comprising the use of a water-soluble polypeptide to treat said disorders and diseases, wherein said water-soluble polypeptide comprises a modified $\alpha$-helical domain, and wherein said water-soluble polypeptide retains the ligand-binding activity of the native membrane protein. Examples of such disorders and diseases include, but are not limited to, cancer, small cell lung cancer, melanoma, breast cancer, Parkinson's disease, cardiovascular disease, hypertension, and asthma.

As described herein, the water-soluble peptides described herein can be used for the treatment of conditions or diseases mediated by the activity of a membrane protein. In certain aspects, the water-soluble peptides can act as "decoys" for the membrane receptor and bind to the ligand that otherwise activates the membrane receptor. As such, the water-soluble peptides described herein can be used to reduce the activity of a membrane protein. These water-soluble peptides can remain in the circulation and competitively bind to specific ligands, thereby reducing the activity of membrane bound receptors.

The invention also encompasses a pharmaceutical composition comprising said water-soluble polypeptide and a pharmaceutically acceptable carrier or diluent.

The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The compositions and pharmacologic agents described herein can be administered in the form of a depot injection or implant preparation which can be formulated in such a manner as to permit a sustained or pulsatile release of the active ingredient.

Transdermal administration includes percutaneous absorption of the composition through the skin. Transdermal formulations include patches, ointments, creams, gels, salves and the like. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

"Treating" or "treatment" includes preventing or delaying the onset of the symptoms, complications, or biochemical indicia of a disease, alleviating or ameliorating the symptoms or arresting or inhibiting further development of the disease, condition, or disorder. A "patient" is a human subject in need of treatment.

An "effective amount" refers to that amount of the therapeutic agent that is sufficient to ameliorate of one or more symptoms of a disorder and/or prevent advancement of a disorder, cause regression of the disorder and/or to achieve a desired effect.

The words "a" or "an" are meant to encompass one or more, unless otherwise specified.

It is to be further understood that where descriptions of various embodiments use the term "comprising," those skilled in the art would understand that in some specific instances, an embodiment can be alternatively described using language "consisting essentially of" or "consisting of."

BAYBUTT, T. R., FLICKINGER, J. C., CAPAROSA, E. M. & SNOOK, A. E. (2019). *Advances in chimeric antigen receptor T-Cell therapies for solid tumors. Clinical Pharmacology & Therapeutics,* 105(1), 71-78.

CACCURI, F., GIAGULLI, C., BUGATTI, A., BENETTI, A., ALESSANDRI, G., RIBATTI, D., MARSICO, S., APOSTOLI, P., SLEVIN, M. A., RUSNATI, M., GUZMAN, C. A., FIORENTINI, S. & CARUSO, A. (2012). *HIV-1 matrix protein p17 promotes angiogenesis via chemokine receptors CXCR1 and CXCR2. Proceedings of the Proc Natl Acad Sci USA,* 109(36), 14580-14585.

CELADA, A., ALLEN, R., ESPARZA, I., GRAY, P. W. & SCHREIBER, R. D. (1985). *Demonstration and partial characterization of the interferon-gamma-receptor on human mononuclear phagocytes. Journal of Clinical Investigation,* 76(6), 2196-2205.

CZAJKOWSKY, D. M., HU, J., SHAO, Z. F. & PLEASS, R. J. (2012). *Fc-fusion proteins: new developments and future perspectives. EMBO Molecular Medicine,* 4(10), 1015-1028.

DE JONG, M. D., SIMMONS, C. P., THANH, T. T., HIEN, V. M., SMITH, G. J. D., CHAU, T. N. B., HOANG, D. M., CHAU, N. V. V., KHANH, T. H., DONG, V. C., QUI, P. T., VAN CAM, B., HA, D. Q., GUAN, Y., PEIRIS, J. S. M., CHINH, N. T., HIEN, T. T. & FARRAR, J. (2006). *Fatal outcome of human influenza A (H5N1) is associated with high viral load and hypercytokinemia. Nature Medicine,* 12(10), 1203-1207.

DRAZEN, J. M. C., R. L.; GOLDMAN, L.; BENNETT, C. (2000). *Cecil textbook of medicine,* 21st edition edition. Philadelphia: W.B. Saunders.

EBERHARDSON, M., KARLEN, P., LINTON, L., JONES, P., LINDBERG, A., KOSTALLA, M. J., LINDH, E., ODEN, A., GLISE, H. & WINQVIST, O. (2017). *Randomised, double-blind, placebo-controlled trial of CCR9-targeted leukapheresis treatment of ulcerative colitis patients. Journal of Crohns & Colitis,* 11(5), 534-542.

HU, Y., ZHANG, L., WU, R. R., HAN, R. F., JIA, Y. H., JIANG, Z. M., CHENG, M. X., GAN, J., TAO, X. & ZHANG, Q. P. (2011). *Specific killing of CCR9 high-expressing acute T lymphocytic leukemia cells by CCL25 fused with PE38 toxin. Leukemia Research,* 35(9), 1254-1260.

HUANG, C., WANG, Y. & LI, X. (2020). *Clinical features of patients infected with 2019 novel coronavirus in Wuhan, China* (vol 395, pg 497, 2020). *Lancet,* 395 (10223), 496-496.

ITTERSHAGEN, S., ERICSON, S., ELDJEROU, L., SHOJAEE, A., BLEICKARDT, E., PATEL, M., TARAN, T., ANAK, O., HALL, C., LEUNG, M., ROCCOBERTON, D., SALMON, F., FUCHS, M., ROMANOV, V. & LEBWOHL, D. (2019). *Industry's giant leap into cellular therapy: catalyzing chimeric antigen receptor T cell (CAR-T) immunotherapy. Current Hematologic Malignancy Reports,* 14(1), 47-55.

JAIN, M. D. & DAVILA, M. L. (2018). *Concise Review: Emerging principles from the clinical application of chimeric antigen receptor t cell therapies for B cell malignancies. Stem Cells,* 36(1), 36-44.

JERABEK-WILLEMSEN, M., ANDRE, T., WANNER, R., ROTH, H. M., DUHR, S., BAASKE, P. & BREITSPRECHER, D. (2014). *MicroScale thermophoresis: interaction analysis and beyond. Journal of Molecular Structure,* 1077, 101-113.

KWON, H. R. (2010). *Study of the structure and function of CXC chemokine receptor 2.* Master's Thesis, University of Tennessee.

LAPORTE, S. L., JUO, Z. S., VACLAVIKOVA, J., COLF, L. A., QI, X. L., HELLER, N. M., KEEGAN, A. D. & GARCIA, K. C. (2008). *Molecular and structural basis of cytokine receptor pleiotropy in the interleukin-4/13 system. Cell,* 132(2), 259-272.

MEKHAIEL, D. N. A., CZAJKOWSKY, D. M., ANDERSEN, J. T., SHI, J. G., EL-FAHAM, M., DOENHOFF, M., MCINTOSH, R. S., SANDLIE, I., HE, J. F., HU, J.,

SHAO, Z. F. & PLEASS, R. J. (2011). *Polymeric human Fc-fusion proteins with modified effector functions*. Scientific Reports, 1.

MIKULECKY, P., CERNY, J., BIEDERMANNOVA, L., PETROKOVA, H., KUCHAR, M., VONDRASEK, J., MALY, P., SEBO, P. & SCHNEIDER, B. (2013). *Increasing affinity of interferon-gamma receptor 1 to interferon-gamma by computer-aided design*. Biomed Research International.

QING, R., HAN, Q. Y., SKUHERSKY, M., CHUNG, H., BADR, M., SCHUBERT, T. & ZHANG, S. G. (2019). *QTY code designed thermostable and water-soluble chimeric chemokine receptors with tunable ligand affinity*. Proc Natl Acad Sci USA, 116(51), 25668-25676.

RAJARATHNAM, K., PRADO, G. N., FERNANDO, H., CLARK-LEWIS, I. & NAVARRO, J. (2006). *Probing receptor binding activity of interleukin-8 dimer using a disulfide trap*. Biochemistry, 45(25), 7882-7888.

RICHTER, D., MORAGA, I., WINKELMANN, H., BIRKHOLZ, O., WILMES, S., SCHULTE, M., KRAICH, M., KENNEWEG, H., BEUTEL, O., SELENSCHIK, P., PATEROK, D., GAVUTIS, M., SCHMIDT, T., GARCIA, K. C., MULLER, T. D. & PIEHLER, J. (2017). *Ligand-induced type II interleukin-4 receptor dimers are sustained by rapid re-association within plasma membrane microcompartments*. Nature Communications, 8, No. 15976.

SAVARIN, C. & BERGMANN, C. C. (2018). *Fine Tuning the Cytokine Storm by IFN and IL-10 Following Neurotropic Coronavirus Encephalomyelitis*. Frontiers in Immunology, 9, 3022.

SHIMABUKURO-VORNHAGEN, A., GODEL, P., SUBKLEWE, M., STEMMLER, H. J., SCHLOSSER, H. A., SCHLAAK, M., KOCHANEK, M., BOLL, B. & VON BERGWELT-BAILDON, M. S. (2018). *Cytokine release syndrome*. Journal for Immunotherapy of Cancer, 6 (1) 56.

SOMOVILLA-CRESPO, B., MONZON, M. T. M., VELA, M., CORRALIZA-GORJON, I., SANTAMARIA, S., GARCIA-SANZ, J. A. & KREMER, L. (2018). *92R monoclonal antibody inhibits human CCR9(+) leukemia cells growth in NSG mice xenografts*. Frontiers in Immunology, 9.

SONNHAMMER, E. L., VON HEIJNE, G. & KROGH, A. (1998). *A hidden Markov model for predicting transmembrane helices in protein sequences*. In Ismb, vol. 6, pp. 175-182.

SRIVASTAVA, S. & RIDDELL, S. R. (2015). *Engineering CAR-T cells: Design concepts*. Trends in Immunology, 36(8), 494-502.

TAN, J. C., INDELICATO, S. R., NARULA, S. K., ZAVODNY, P. J. & CHOU, C. C. (1993). *Characterization of interleukin-10 receptors on human and mouse cells*. J. Biological Chemistry, 268(28), 21053-21059.

TISONCIK, J. R., KORTH, M. J., SIMMONS, C. P., FARRAR, J., MARTIN, T. R. & KATZE, M. G. (2012). *Into the eye of the cytokine storm*. Microbiology and Molecular Biology Reviews, 76(1), 16-32.

TU, Z. B., XIAO, R. J., XIONG, J., TEMBO, K. M., DENG, X. Z., XIONG, M., LIU, P., WANG, M. & ZHANG, Q. P. (2016). *CCR9 in cancer: oncogenic role and therapeutic targeting*. J. Hematology & Oncology, 9:10 doi: 10.1186/s13045-016-0236-7.

XU, X. J. & TANG, Y. M. (2014). *Cytokine release syndrome in cancer immunotherapy with chimeric antigen receptor engineered T cells*. Cancer Letters, 343(2), 172-178.

XU, Z., SHI, L., WANG, Y., ZHANG, J., HUANG, L., ZHANG, C., LIU, S., ZHAO, P., LIU, H. & ZHU, L. (2020). *Pathological findings of COVID-19 associated with acute respiratory distress syndrome*. The Lancet Respiratory Medicine. pii: S2213-2600(20)30076-X. doi: 10.1016/S2213-2600(20)30076-X.

ZHANG, S. G., TAO, F., QING, R., TANG, H. Z., SKUHERSKY, M., CORIN, K., TEGLER, L., WASSIE, A., WASSIE, B., KWON, Y., SUTER, B., ENTZIAN, C., SCHUBERT, T., YANG, G., LABAHN, J., KUBICEK, J. & MAERTENS, B. (2018). *QTY code enables design of detergent-free chemokine receptors that retain ligand-binding activities*. Proc Natl Acad Sci USA, 115(37), E8652-E8659.

All documents and references described herein are individually incorporated by reference to into this document to the same extent as if there were written in this document in full or in part.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

While this invention has been particularly shown and described with references to preferred embodiments thereof, it will be understood by those skilled in the art that various changes in form and details may be made therein without departing from the scope of the invention encompassed by the appended claims.

What is claimed is:

1. A Fc fusion human CCR9 receptor protein variant comprising a Fc domain and one or more QTY CCR9 variant receptor domains wherein each transmembrane region of human CCR9 receptor protein comprises the amino acid sequence of human CCR9 transmembrane domain in which each of the internal L, V, I and Fs in each transmembrane domain of human CCR9 receptor are replaced with Q, T, T and Y, respectively.

2. The Fc fusion QTY CCR9 variant receptor protein of claim 1, wherein the Fc domain comprises an IgG constant domain.

3. The Fc fusion QTY CCR9 variant receptor protein of claim 1, wherein the Fc Domain is fused to the QTY CCR9 variant receptor domain via a hinge region.

* * * * *

SEQUENCE LISTING

```
<160> NUMBER OF SEQ ID NOS: 7

<210> SEQ ID NO 1
<211> LENGTH: 369
<212> TYPE: PRT
<213> ORGANISM: Artificial Sequence
<220> FEATURE:
<223> OTHER INFORMATION: CCR-9

<400> SEQUENCE: 1

Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
            20                  25                  30
```

Phe Thr Asp Phe Tyr Cys Glu Lys Asn Asn Val Arg Gln Phe Ala Ser
            35                  40                  45

His Tyr Gln Pro Pro Gln Tyr Trp Gln Thr Tyr Thr Thr Gly Ala Gln
 50                  55                  60

Gly Asn Ser Gln Thr Thr Gln Thr Tyr Trp Tyr Cys Thr Arg Val Lys
 65                  70                  75                  80

Thr Met Thr Asp Met Tyr Gln Gln Asn Gln Ala Thr Ala Asp Gln Gln
                85                  90                  95

Tyr Gln Thr Thr Gln Pro Tyr Trp Ala Thr Ala Ala Asp Gln Trp
            100                 105                 110

Lys Phe Gln Thr Phe Met Cys Lys Thr Thr Asn Ser Met Tyr Lys Met
            115                 120                 125

Asn Tyr Tyr Ser Cys Thr Gln Gln Thr Met Cys Thr Ser Thr Asp Arg
            130                 135                 140

Tyr Thr Ala Thr Ala Gln Ala Met Arg Ala His Thr Trp Arg Glu Lys
145                 150                 155                 160

Arg Gln Gln Tyr Ser Lys Met Thr Cys Tyr Thr Thr Trp Thr Gln Ala
                165                 170                 175

Ala Ala Gln Cys Thr Pro Glu Thr Gln Tyr Ser Gln Ile Lys Glu Glu
            180                 185                 190

Ser Gly Ile Ala Ile Cys Thr Met Val Tyr Pro Ser Asp Glu Ser Thr
            195                 200                 205

Lys Gln Lys Ser Ala Thr Gln Thr Gln Lys Thr Thr Gln Gly Tyr Tyr
            210                 215                 220

Gln Pro Tyr Thr Thr Met Ala Cys Cys Tyr Thr Thr Thr His Thr
225                 230                 235                 240

Gln Thr Gln Ala Lys Lys Ser Ser Lys His Lys Ala Gln Lys Thr Thr
                245                 250                 255

Thr Thr Thr Gln Thr Thr Tyr Thr Gln Ser Gln Tyr Pro Tyr Asn Cys
            260                 265                 270

Thr Gln Gln Thr Gln Thr Thr Asp Ala Tyr Ala Met Phe Ile Ser Asn
            275                 280                 285

Cys Ala Thr Ser Thr Asn Thr Asp Thr Cys Tyr Gln Thr Thr Gln Thr
290                 295                 300

Thr Ala Tyr Tyr His Ser Cys Gln Asn Pro Thr Gln Tyr Thr Tyr Thr
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
            340                 345                 350

Leu Lys Leu Ser Ser Met Leu Leu Glu Thr Thr Ser Gly Ala Leu Ser
            355                 360                 365

Leu

<210> SEQ ID NO 2
<211> LENGTH: 369
<212> TYPE: PRT
<213> ORGANISM: Homo sapiens

<400> SEQUENCE: 2

Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
            20                  25                  30

```
Phe Thr Asp Phe Tyr Cys Glu Lys Asn Asn Val Arg Gln Phe Ala Ser
         35                  40                  45

His Phe Leu Pro Pro Leu Tyr Trp Leu Val Phe Ile Val Gly Ala Leu
 50                  55                  60

Gly Asn Ser Leu Val Ile Leu Val Tyr Trp Tyr Cys Thr Arg Val Lys
 65                  70                  75                  80

Thr Met Thr Asp Met Phe Leu Leu Asn Leu Ala Ile Ala Asp Leu Leu
                 85                  90                  95

Phe Leu Val Thr Leu Pro Phe Trp Ala Ile Ala Ala Asp Gln Trp
                100                 105                 110

Lys Phe Gln Thr Phe Met Cys Lys Val Val Asn Ser Met Tyr Lys Met
                115                 120                 125

Asn Phe Tyr Ser Cys Val Leu Leu Ile Met Cys Ile Ser Val Asp Arg
                130                 135                 140

Tyr Ile Ala Ile Ala Gln Ala Met Arg Ala His Thr Trp Arg Glu Lys
145                 150                 155                 160

Arg Leu Leu Tyr Ser Lys Met Val Cys Phe Thr Ile Trp Val Leu Ala
                165                 170                 175

Ala Ala Leu Cys Ile Pro Glu Ile Leu Tyr Ser Gln Ile Lys Glu Glu
                180                 185                 190

Ser Gly Ile Ala Ile Cys Thr Met Val Tyr Pro Ser Asp Glu Ser Thr
                195                 200                 205

Lys Leu Lys Ser Ala Val Leu Thr Leu Lys Val Ile Leu Gly Phe Phe
                210                 215                 220

Leu Pro Phe Val Val Met Ala Cys Cys Tyr Thr Ile Ile His Thr
225                 230                 235                 240

Leu Ile Gln Ala Lys Lys Ser Ser Lys His Lys Ala Leu Lys Val Thr
                245                 250                 255

Ile Thr Val Leu Thr Val Phe Val Leu Ser Gln Phe Pro Tyr Asn Cys
                260                 265                 270

Ile Leu Leu Val Gln Thr Ile Asp Ala Tyr Ala Met Phe Ile Ser Asn
                275                 280                 285

Cys Ala Val Ser Thr Asn Ile Asp Ile Cys Phe Gln Val Thr Gln Thr
                290                 295                 300

Ile Ala Phe Phe His Ser Cys Leu Asn Pro Val Leu Tyr Val Phe Val
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
                340                 345                 350

Leu Lys Leu Ser Ser Met Leu Leu Glu Thr Thr Ser Gly Ala Leu Ser
                355                 360                 365

Leu
```

<210> SEQ ID NO 3
<211> LENGTH: 369
<212> TYPE: PRT
<213> ORGANISM: Artificial Sequence
<220> FEATURE:
<223> OTHER INFORMATION: CXCR2

<400> SEQUENCE: 3

```
Met Thr Pro Thr Asp Phe Thr Ser Pro Ile Pro Asn Met Ala Asp Asp
 1               5                  10                  15
```

-continued

```
Tyr Gly Ser Glu Ser Thr Ser Ser Met Glu Asp Tyr Val Asn Phe Asn
                20                  25                  30
Phe Thr Asp Phe Tyr Cys Glu Lys Asn Asn Val Arg Gln Phe Ala Ser
            35                  40                  45
His Tyr Gln Pro Pro Gln Tyr Trp Gln Thr Tyr Thr Thr Gly Ala Gln
        50                  55                  60
Gly Asn Ser Gln Thr Thr Gln Thr Tyr Trp Tyr Cys Thr Arg Val Lys
65                  70                  75                  80
Thr Met Thr Asp Met Tyr Gln Gln Asn Gln Ala Thr Ala Asp Gln Gln
                85                  90                  95
Tyr Gln Thr Thr Gln Pro Tyr Trp Ala Thr Ala Ala Asp Gln Trp
            100                 105                 110
Lys Phe Gln Thr Phe Met Cys Lys Thr Thr Asn Ser Met Tyr Lys Met
        115                 120                 125
Asn Tyr Tyr Ser Cys Thr Gln Gln Thr Met Cys Thr Ser Thr Asp Arg
            130                 135                 140
Tyr Thr Ala Thr Ala Gln Ala Met Arg Ala His Thr Trp Arg Glu Lys
145                 150                 155                 160
Arg Gln Gln Tyr Ser Lys Met Thr Cys Tyr Thr Thr Trp Thr Gln Ala
                165                 170                 175
Ala Ala Gln Cys Thr Pro Glu Thr Gln Tyr Ser Gln Ile Lys Glu Glu
            180                 185                 190
Ser Gly Ile Ala Ile Cys Thr Met Val Tyr Pro Ser Asp Glu Ser Thr
        195                 200                 205
Lys Gln Lys Ser Ala Thr Gln Thr Gln Lys Thr Thr Gln Gly Tyr Tyr
    210                 215                 220
Gln Pro Tyr Thr Thr Met Ala Cys Cys Tyr Thr Thr Thr His Thr
225                 230                 235                 240
Gln Thr Gln Ala Lys Lys Ser Ser Lys His Lys Ala Gln Lys Thr Thr
                245                 250                 255
Thr Thr Thr Gln Thr Thr Tyr Thr Gln Ser Gly Tyr Pro Tyr Asn Cys
            260                 265                 270
Thr Gln Gln Thr Gln Thr Thr Asp Ala Tyr Ala Met Phe Ile Ser Asn
        275                 280                 285
Cys Ala Thr Ser Thr Asn Thr Asp Thr Cys Tyr Gln Thr Thr Gln Thr
    290                 295                 300
Thr Ala Tyr Tyr His Ser Cys Gln Asn Pro Thr Gln Tyr Thr Tyr Thr
305                 310                 315                 320
Gly Glu Arg Phe Arg Arg Asp Leu Val Lys Thr Leu Lys Asn Leu Gly
                325                 330                 335
Cys Ile Ser Gln Ala Gln Trp Val Ser Phe Thr Arg Arg Glu Gly Ser
            340                 345                 350
Leu Lys Leu Ser Ser Met Leu Leu Glu Thr Thr Ser Gly Ala Leu Ser
        355                 360                 365
Leu
```

<210> SEQ ID NO 4
<211> LENGTH: 369
<212> TYPE: PRT
<213> ORGANISM: Homo sapiens

<400> SEQUENCE: 4

```
Met Thr Pro Thr Asp Phe Thr Ser Pro Ile Pro Asn Met Ala Asp Asp
1               5                   10                  15
```

```
Tyr Gly Ser Glu Ser Thr Ser Ser Met Glu Asp Tyr Val Asn Phe Asn
             20                  25                  30
Phe Thr Asp Phe Tyr Cys Glu Lys Asn Asn Val Arg Gln Phe Ala Ser
         35                  40                  45
His Phe Leu Pro Pro Leu Tyr Trp Leu Val Phe Ile Val Gly Ala Leu
 50                  55                  60
Gly Asn Ser Leu Val Ile Leu Val Tyr Trp Tyr Cys Thr Arg Val Lys
 65                  70                  75                  80
Thr Met Thr Asp Met Phe Leu Leu Asn Leu Ala Ile Ala Asp Leu Leu
                 85                  90                  95
Phe Leu Val Thr Leu Pro Phe Trp Ala Ile Ala Ala Asp Gln Trp
            100                 105                 110
Lys Phe Gln Thr Phe Met Cys Lys Val Val Asn Ser Met Tyr Lys Met
        115                 120                 125
Asn Phe Tyr Ser Cys Val Leu Leu Ile Met Cys Ile Ser Val Asp Arg
        130                 135                 140
Tyr Ile Ala Ile Ala Gln Ala Met Arg Ala His Thr Trp Arg Glu Lys
145                 150                 155                 160
Arg Leu Leu Tyr Ser Lys Met Val Cys Phe Thr Ile Trp Val Leu Ala
                165                 170                 175
Ala Ala Leu Cys Ile Pro Glu Ile Leu Tyr Ser Gln Ile Lys Glu Glu
            180                 185                 190
Ser Gly Ile Ala Ile Cys Thr Met Val Tyr Pro Ser Asp Glu Ser Thr
        195                 200                 205
Lys Leu Lys Ser Ala Val Leu Thr Leu Lys Val Ile Leu Gly Phe Phe
210                 215                 220
Leu Pro Phe Val Val Met Ala Cys Cys Tyr Thr Ile Ile His Thr
225                 230                 235                 240
Leu Ile Gln Ala Lys Lys Ser Ser Lys His Lys Ala Leu Lys Val Thr
                245                 250                 255
Ile Thr Val Leu Thr Val Phe Val Leu Ser Gln Phe Pro Tyr Asn Cys
            260                 265                 270
Ile Leu Leu Val Gln Thr Ile Asp Ala Tyr Ala Met Phe Ile Ser Asn
        275                 280                 285
Cys Ala Val Ser Thr Asn Ile Asp Ile Cys Phe Gln Val Thr Gln Thr
    290                 295                 300
Ile Ala Phe Phe His Ser Cys Leu Asn Pro Val Leu Tyr Val Phe Val
305                 310                 315                 320
Gly Glu Arg Phe Arg Arg Asp Leu Val Lys Thr Leu Lys Asn Leu Gly
                325                 330                 335
Cys Ile Ser Gln Ala Gln Trp Val Ser Phe Thr Arg Arg Glu Gly Ser
            340                 345                 350
Leu Lys Leu Ser Ser Met Leu Leu Glu Thr Thr Ser Gly Ala Leu Ser
        355                 360                 365
Leu

<210> SEQ ID NO 5
<211> LENGTH: 23
<212> TYPE: PRT
<213> ORGANISM: Artificial Sequence
<220> FEATURE:
<223> OTHER INFORMATION: Synthetic

<400> SEQUENCE: 5

Pro Arg Gly Pro Thr Ile Lys Pro Cys Pro Pro Cys Lys Cys Pro Ala
```

```
1               5                   10                  15
Pro Asn Leu Gly Gly Pro
            20
```

<210> SEQ ID NO 6
<211> LENGTH: 645
<212> TYPE: PRT
<213> ORGANISM: Artificial Sequence
<220> FEATURE:
<223> OTHER INFORMATION: CCR9- QTY Fc

<400> SEQUENCE: 6

```
Met Thr Pro Thr Asp Phe Thr Ser Pro Ile Pro Asn Met Ala Asp Asp
1               5                   10                  15

Tyr Gly Ser Glu Ser Thr Ser Ser Met Glu Asp Tyr Val Asn Phe Asn
            20                  25                  30

Phe Thr Asp Phe Tyr Cys Glu Lys Asn Asn Val Arg Gln Phe Ala Ser
        35                  40                  45

His Tyr Gln Pro Pro Gln Tyr Trp Gln Thr Tyr Thr Thr Gly Ala Gln
    50                  55                  60

Gly Asn Ser Gln Thr Thr Gln Thr Tyr Trp Tyr Cys Thr Arg Val Lys
65                  70                  75                  80

Thr Met Thr Asp Met Tyr Gln Gln Asn Gln Ala Thr Ala Asp Gln Gln
                85                  90                  95

Tyr Gln Thr Thr Gln Pro Tyr Trp Ala Thr Ala Ala Asp Gln Trp
            100                 105                 110

Lys Phe Gln Thr Phe Met Cys Lys Thr Thr Asn Ser Met Tyr Lys Met
        115                 120                 125

Asn Tyr Tyr Ser Cys Thr Gln Gln Thr Met Cys Thr Ser Thr Asp Arg
    130                 135                 140

Tyr Thr Ala Thr Ala Gln Ala Met Arg Ala His Thr Trp Arg Glu Lys
145                 150                 155                 160

Arg Gln Gln Tyr Ser Lys Met Thr Cys Tyr Thr Thr Trp Thr Gln Ala
                165                 170                 175

Ala Ala Gln Cys Thr Pro Glu Thr Gln Tyr Ser Gln Ile Lys Glu Glu
            180                 185                 190

Ser Gly Ile Ala Ile Cys Thr Met Val Tyr Pro Ser Asp Glu Ser Thr
        195                 200                 205

Lys Gln Lys Ser Ala Thr Gln Thr Lys Thr Thr Gln Gly Tyr Tyr
    210                 215                 220

Gln Pro Tyr Thr Thr Met Ala Cys Cys Tyr Thr Thr Thr His Thr
225                 230                 235                 240

Gln Thr Gln Ala Lys Lys Ser Ser Lys His Lys Ala Gln Lys Thr Thr
                245                 250                 255

Thr Thr Thr Gln Thr Thr Tyr Thr Gln Ser Gln Tyr Pro Tyr Asn Cys
            260                 265                 270

Thr Gln Gln Thr Gln Thr Asp Ala Tyr Ala Met Phe Ile Ser Asn
        275                 280                 285

Cys Ala Thr Ser Thr Asn Thr Asp Thr Cys Tyr Gln Thr Thr Gln Thr
    290                 295                 300

Thr Ala Tyr Tyr His Ser Cys Gln Asn Pro Gln Tyr Thr Tyr Thr
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
```

```
              340                 345                 350
Leu Lys Leu Ser Ser Met Leu Leu Glu Thr Thr Ser Gly Ala Leu Ser
            355                 360                 365

Leu Thr Glu Thr Ser Gln Val Ala Pro Ala His His His His His His
        370                 375                 380

His His His His Thr Glu Thr Ser Gln Val Ala Pro Ala His His His
385                 390                 395                 400

His His His His His His Gly Ser Lys Leu Val Asp Pro Arg Gly
                    405                 410                 415

Pro Thr Ile Lys Pro Cys Pro Pro Cys Lys Cys Pro Ala Pro Asn Leu
                420                 425                 430

Leu Gly Gly Pro Ser Val Phe Ile Phe Pro Pro Lys Ile Lys Asp Val
            435                 440                 445

Leu Met Ile Ser Leu Ser Pro Ile Val Thr Cys Val Val Val Asp Val
        450                 455                 460

Ser Glu Asp Asp Pro Asp Val Gln Ile Ser Trp Phe Val Asn Asn Val
465                 470                 475                 480

Glu Val His Thr Ala Gln Thr Gln Thr His Arg Glu Asp Tyr Asn Ser
                485                 490                 495

Thr Leu Arg Val Val Ser Ala Leu Pro Ile Gln His Gln Asp Trp Met
                500                 505                 510

Ser Gly Lys Glu Phe Lys Cys Lys Val Asn Asn Lys Asp Leu Pro Ala
            515                 520                 525

Pro Ile Glu Arg Thr Ile Ser Lys Pro Lys Gly Ser Val Arg Ala Pro
        530                 535                 540

Gln Val Tyr Val Leu Pro Pro Pro Glu Glu Glu Met Thr Lys Lys Gln
545                 550                 555                 560

Val Thr Leu Thr Cys Met Val Thr Asp Phe Met Pro Glu Asp Ile Tyr
                565                 570                 575

Val Glu Trp Thr Asn Asn Gly Lys Thr Glu Leu Asn Tyr Lys Asn Thr
            580                 585                 590

Glu Pro Val Leu Asp Ser Asp Gly Ser Tyr Phe Met Tyr Ser Lys Leu
        595                 600                 605

Arg Val Glu Lys Lys Asn Trp Val Glu Arg Asn Ser Tyr Ser Cys Ser
    610                 615                 620

Val Val His Glu Gly Leu His Asn His His Thr Thr Lys Ser Phe Ser
625                 630                 635                 640

Arg Thr Pro Gly Lys
                645

<210> SEQ ID NO 7
<211> LENGTH: 617
<212> TYPE: PRT
<213> ORGANISM: Artificial Sequence
<220> FEATURE:
<223> OTHER INFORMATION: CXCR2-QTY Fc

<400> SEQUENCE: 7

Met Glu Asp Phe Asn Met Glu Ser Asp Ser Phe Glu Asp Phe Trp Lys
1               5                   10                  15

Gly Glu Asp Leu Ser Asn Tyr Ser Tyr Ser Ser Thr Leu Pro Pro Phe
            20                  25                  30

Leu Leu Asp Ala Ala Pro Cys Glu Pro Glu Ser Leu Glu Ile Asn Lys
        35                  40                  45

Tyr Tyr Thr Thr Thr Thr Tyr Ala Gln Thr Tyr Gln Gln Ser Gln Gln
```

```
                50                  55                  60
Gly Asn Ser Gln Thr Met Gln Thr Thr Gln Tyr Ser Arg Val Gly Arg
 65                  70                  75                  80

Ser Val Thr Asp Thr Tyr Gln Asn Gln Ala Gln Ala Asp Gln Gln
                 85                  90                  95

Tyr Ala Gln Thr Gln Pro Thr Trp Ala Ser Lys Val Asn Gly Trp
                100                 105                 110

Ile Phe Gly Thr Phe Leu Cys Lys Thr Thr Ser Gln Gln Lys Glu Thr
                115                 120                 125

Asn Tyr Tyr Ser Gly Thr Gln Gln Gln Ala Cys Thr Ser Thr Asp Arg
130                 135                 140

Tyr Leu Ala Ile Val His Ala Thr Arg Thr Leu Thr Gln Lys Arg Tyr
145                 150                 155                 160

Leu Val Lys Tyr Thr Cys Gln Ser Thr Trp Gly Gln Ser Gln Gln Gln
                165                 170                 175

Ala Gln Pro Thr Gln Gln Tyr Arg Arg Thr Val Tyr Ser Ser Asn Val
                180                 185                 190

Ser Pro Ala Cys Tyr Glu Asp Met Gly Asn Asn Thr Ala Asn Trp Arg
                195                 200                 205

Met Gln Gln Arg Thr Gln Pro Gln Ser Tyr Gly Tyr Thr Gln Pro Gln
210                 215                 220

Gln Thr Met Gln Tyr Cys Tyr Gly Phe Thr Leu Arg Thr Leu Phe Lys
225                 230                 235                 240

Ala His Met Gly Gln Lys His Arg Ala Met Arg Thr Thr Tyr Ala Thr
                245                 250                 255

Thr Gln Thr Tyr Gln Gln Cys Trp Gln Pro Tyr Asn Gln Thr Gln Gln
                260                 265                 270

Ala Asp Thr Leu Met Arg Thr Gln Val Ile Gln Glu Thr Cys Glu Arg
                275                 280                 285

Arg Asn His Ile Asp Arg Ala Gln Asp Ala Thr Glu Thr Gln Gly Thr
290                 295                 300

Gln His Ser Cys Gln Asn Pro Gln Thr Tyr Ala Tyr Thr Gly Gln Lys
305                 310                 315                 320

Phe Arg His Gly Leu Leu Lys Ile Leu Ala Ile His Gly Leu Ile Ser
                325                 330                 335

Lys Asp Ser Leu Pro Lys Asp Ser Arg Pro Ser Phe Val Gly Ser Ser
                340                 345                 350

Ser Gly His Thr Ser Thr Thr Leu Thr Glu Thr Ser Gln Val Ala Pro
                355                 360                 365

Ala His His His His His His His His Gly Ser Lys Leu Val
                370                 375                 380

Asp Pro Arg Gly Pro Thr Ile Lys Pro Cys Pro Pro Cys Lys Cys Pro
385                 390                 395                 400

Ala Pro Asn Leu Leu Gly Gly Pro Ser Val Phe Ile Phe Pro Pro Lys
                405                 410                 415

Ile Lys Asp Val Leu Met Ile Ser Leu Ser Pro Ile Val Thr Cys Val
                420                 425                 430

Val Val Asp Val Ser Glu Asp Pro Asp Val Gln Ile Ser Trp Phe
                435                 440                 445

Val Asn Asn Val Glu Val His Thr Ala Gln Thr Gln Thr His Arg Glu
450                 455                 460

Asp Tyr Asn Ser Thr Leu Arg Val Val Ser Ala Leu Pro Ile Gln His
465                 470                 475                 480
```

```
Gln Asp Trp Met Ser Gly Lys Glu Phe Lys Cys Lys Val Asn Asn Lys
                485                 490                 495
Asp Leu Pro Ala Pro Ile Glu Arg Thr Ile Ser Lys Pro Lys Gly Ser
                500                 505                 510
Val Arg Ala Pro Gln Val Tyr Val Leu Pro Pro Pro Glu Glu Glu Met
                515                 520                 525
Thr Lys Lys Gln Val Thr Leu Thr Cys Met Val Thr Asp Phe Met Pro
                530                 535                 540
Glu Asp Ile Tyr Val Glu Trp Thr Asn Asn Gly Lys Thr Glu Leu Asn
545                 550                 555                 560
Tyr Lys Asn Thr Glu Pro Val Leu Asp Ser Asp Gly Ser Tyr Phe Met
                565                 570                 575
Tyr Ser Lys Leu Arg Val Glu Lys Lys Asn Trp Val Glu Arg Asn Ser
                580                 585                 590
Tyr Ser Cys Ser Val Val His Glu Gly Leu His Asn His His Thr Thr
                595                 600                 605
Lys Ser Phe Ser Arg Thr Pro Gly Lys
                610                 615
```

UNITED STATES PATENT AND TRADEMARK OFFICE
CERTIFICATE OF CORRECTION

PATENT NO. : 11,401,320 B2
APPLICATION NO. : 17/210878
DATED : August 2, 2022
INVENTOR(S) : Shuguang Zhang et al.

It is certified that error appears in the above-identified patent and that said Letters Patent is hereby corrected as shown below:

On the Title Page

(73) Assignees:
Please delete "Avalong GloboCare Corp., Freehold, NJ (US)" and replace with
--Avalon GloboCare Corp., Freehold, NJ (US)--.

Signed and Sealed this
Fifteenth Day of November, 2022

Katherine Kelly Vidal
*Director of the United States Patent and Trademark Office*